(12) United States Patent
Shi

(10) Patent No.: US 7,282,355 B2
(45) Date of Patent: Oct. 16, 2007

(54) NUCLEIC ACID DETECTION METHOD

(75) Inventor: Liang Shi, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 352 days.

(21) Appl. No.: 10/388,329

(22) Filed: Mar. 13, 2003

(65) Prior Publication Data

US 2004/0002093 A1  Jan. 1, 2004

Related U.S. Application Data

(60) Provisional application No. 60/364,230, filed on Mar. 13, 2002.

(51) Int. Cl.
*C12P 19/34* (2006.01)
*C12Q 1/68* (2006.01)
*C07H 21/02* (2006.01)
*C07H 21/04* (2006.01)

(52) U.S. Cl. .................. 435/91.2; 435/6; 435/91.1; 536/23.1; 536/24.3; 536/24.33; 536/25.3

(58) Field of Classification Search ............ 435/6, 435/91.1, 91.2, 91.51, 183; 436/94; 536/23.1, 536/24.3, 24.33, 25.3, 25.32
See application file for complete search history.

(56) References Cited

U.S. PATENT DOCUMENTS

| | | | |
|---|---|---|---|
| 5,679,524 A | 10/1997 | Nikiforov et al. ............ | 435/6 |
| 5,736,330 A | 4/1998 | Fulton ......................... | 435/6 |
| 5,770,365 A | 6/1998 | Lane et al. ................... | 435/6 |
| 5,800,994 A | 9/1998 | Martinelli et al. ........... | 435/6 |
| 5,830,711 A | 11/1998 | Barany et al. ............. | 435/91.1 |
| 5,837,860 A | 11/1998 | Anderson et al. .......... | 536/25.3 |
| 5,863,722 A | 1/1999 | Brenner ....................... | 435/6 |
| 5,866,337 A | 2/1999 | Schon ......................... | 435/6 |
| 5,914,229 A | 6/1999 | Loewy ......................... | 435/6 |
| 6,013,431 A | 1/2000 | Söderlund et al. ........... | 435/5 |
| 6,020,137 A | 2/2000 | Lapidus et al. .............. | 435/6 |
| 6,027,889 A | 2/2000 | Barany et al. ............... | 435/6 |
| 6,030,782 A | 2/2000 | Anderson et al. ........... | 435/6 |
| 6,057,107 A | 5/2000 | Fulton ......................... | 435/6 |
| 6,140,489 A | 10/2000 | Brenner ..................... | 536/24.3 |
| 6,150,516 A | 11/2000 | Brenner et al. ............ | 536/24.3 |
| 6,172,214 B1 | 1/2001 | Brenner ..................... | 536/24.3 |
| 6,172,218 B1 | 1/2001 | Brenner ..................... | 536/25.4 |
| 6,184,000 B1 | 2/2001 | Jones et al. ............... | 435/91.41 |

FOREIGN PATENT DOCUMENTS

| | | |
|---|---|---|
| GB | 2295011 | 5/1996 |
| GB | 2295228 | 5/1996 |
| WO | WO96/15271 | 5/1996 |
| WO | WO96/31622 | 10/1996 |
| WO | WO99/22030 | 5/1999 |
| WO | WO99/67414 | 12/1999 |
| WO | WO99/67641 | 12/1999 |
| WO | WO00/24939 | 5/2000 |
| WO | WO00/39345 | 7/2000 |
| WO | WO00/39587 | 7/2000 |
| WO | WO00/40755 | 7/2000 |
| WO | WO00/47996 | 8/2000 |
| WO | WO00/48000 | 8/2000 |
| WO | WO00/53806 | 9/2000 |
| WO | WO00/67894 | 11/2000 |
| WO | WO01/11333 | 2/2001 |
| WO | WO01/13120 | 2/2001 |
| WO | WO01/18524 | 3/2001 |
| WO | WO 01/61033 | 8/2001 |
| WO | WO 01/92579 | 12/2001 |
| WO | WO 03/002762 | 1/2003 |
| WO | WO 03/052140 | 6/2003 |

OTHER PUBLICATIONS

European Search Report corresponding to European Application No. 0376551.1 dated Oct. 6, 2005.
Shi Michael M., "EnablinG Large-Scale Pharmacogenetic Studies by High-Throughput Mutation Detection and Genotyping Technologies", *Clinical Chemistry*, 47 (2): 164-172, 2001.
Iannone et al., "Multiplexed Single Nucleotide Polymorphism Genotyping by Oligonucleotide Ligation and Flow Cytometry", *Cytometry*, 39; 131-140, 2000.
Notification of Transmittal of International Preliminary Examination Report corresponding to PCT Application Serial No. PCT/US03/07818 dated Oct. 17, 2006.
Communication pursuant to Article 96(2) EPC corresponding to EP Patent Application No. 03716551.1 dated Sep. 20, 2006.

*Primary Examiner*—Frank Lu
(74) *Attorney, Agent, or Firm*—Jenkins, Wilson, Taylor & Hunt, P.A.

(57) ABSTRACT

Disclosed are methods for detecting a target nucleic acid molecule having a known sequence among a plurality of nucleic acid molecules. The method includes hybridizing two oligonucleotides to adjacent nucleotide sequences on the target nucleic acid molecule, ligating the two oligonucleotides together, and extending a primer that hybrizes to the 3' end of the oligonucleotide that hybrized to the 5' nucleotide sequence on the target nucleic acid molecule. If the target nucleic acid molecule is present (and thereby allowing ligation of the two oligonucleotides), extension of the primer dislodges a detection probe hybridized to the 5' end of the oligonucleotide that hybridized to the 3' nucleotide sequence on the target nucleic acid molecule.

Also disclosed are kits for performing the methods of the invention.

23 Claims, 4 Drawing Sheets

```
1    ccgcagaagc tcggccttcc cgtcggcagg cacgtgtacg tgtgcgcgtc gataggcggc
61   aagctctgca tgcgcgcgta cacgcccacg agcccgtcg  acgaggtcgg ccacttcgat
121  ctcctcatca agatatactt caaggacgag gaccccaagt accccaacgg cgggctcatg
181  tcgcagtacc tggactccct gccgctgggc gcgactattg acatcaaggg tccgcatagg
241  cacatcgagt acaccggccg ccgccgcttc gtggtgaacg gcaagcagcg tcacgcgcgc
301  aggctcgcca tgatccaggc cggcagaggg accacgcccg acgacgacac ggagcaggcc
361  gtgctgaggg accagcccga cgacgacacg gagatgcacc tcgtgtacgc gaaccgaacg
421  gaccacgaca tgctcctaag ggaggagatc gaccgcgctt ggctgccgcg caccccggcgc
481  ctcaaggtgt ggtacgtggt cagcaaggtc ccggaggacg ggtgggagta cggcgtgggg
541  agagtggacg agcatgtcat gagggagcac ctgcctctgg gagacagcga gaccattgcg
601  ctcgtgtgcg ggccgccggc gatgatcgag tgcacagtgc gcccgggcct ggagaagatg
661  gggtacgacc tcgacaaggc ttgtctcgtg ttctgagctc tgaatagcgg ctaacggatg
721  tcgtcaaggt gcaactgtac atagaaattc tgtggtgcct tgaatcttga accctagtaa
781  cgtgtcgatc tagctagaac tctaccgagt tctcttgtaa tactagcgat ttaaactggc
841  catggaagtt catactagct ggtgccatgg ccgtcttgtc aagatgagat gtattggtcc
901  tactatatac agcgcaataa aaaccccaag g
```

Figure 3

```
   1 acgaggtttc acacatagct tcgtcgattt gaatttgatg tactaatgga gtctaagggt
  61 ggcaaaaagt ctagcagtag tcgttctatg atgtatgaag ctcccttgg ctacagcatt
 121 gaggacgttc gacctgccgg aggcgtgaag aagttccagt ctgctgctta ctccaactgc
 181 gcgaagaagc catcctgata tccctttgg cttcctcatt ctagtagttt aggatttctt
 241 ttctgacact ttgattctga ccaatctctc tggcctgctg cttcctgata atcgaccagt
 301 tccccagtct tgctccttgc actcctccct ccatctccag cattgtgttc tgattcacct
 361 gctccaatgg ctgttctttc tgctgctgat gcttccccgg tctcagctat cgggtttgag
 421 ggctatgaga agcgccttga gatcacattc tctgaggcac ctgtctttgt ggaccctcat
 481 gggcgtggtt tgcgtgccct ctccagggcc cagattgact ctgttctgga tcttgcacgg
 541 tgcacaattg tgtctgagct ctccaacaag gatttcgact catatgtcct ttctgagtca
 601 agcttgttta tctatcctct gaagattgtc atcaagacct gtggcactac caagctcctg
 661 ctcaccattc caagaatcct tgagcttgct gaagagctgt ctatgccact tgctgctgtg
 721 aagtactccc gtgggacgtt catctttcct ggcgcacagc cagcccccca caggagcttc
 781 tctgaggaag ttgctgcact taaccgctac tttggcggcc tgaaatctgg tggtaatgct
 841 tatgtgattg gagatccagc aagacctgga cagaagtggc acgtcttcta cgccactgag
 901 tacccagagc aaccaatggt taaccttgag atgtgcatga ctggtctgga caagaagaaa
 961 gcttgtgtct ttttcaagac taatgctgat gggaacacaa catgtgccaa ggaaatgaca
1021 aagctctctg gcatctctga atcatcccc gagatggaga tctgcgattt tgacttcgaa
1081 ccctgtggct actccatgaa tgcgatccat ggctctgcat tctccacaat ccatgtgacg
1141 cccgaggacg gtttcagcta cgccagttac gaggttatgg gcttggatgc cactgctctg
1201 tcttatggtg accttgtcaa gagggtcctc cggtgctttg gcccctcaga gttttccgtt
1261 gccgtgacca tcttcggcgg cgtggccat gccgggacat ggggaaaggc acttggtgca
1321 gaggtctatg actgcaacaa catggtggag caggagctgc ctggaggcgg gctcctcgtg
1381 taccagagct tctgtgctgc tgaagacgct gttgctacct cgcccaaatc tgttttccac
1441 tgctttgacg gcgagaacgt ggagagtgct cctcctccta tgaagaagga ctacaagctg
1501 gctaatcttc tctgctggga ggaggaagcg gatgccatgg aggagaaggc gggagtgctt
1561 gatgagtaag acgggcttct ggggtcgatt tgcttctgag ttgtttattt tatatcgtcg
1621 caatttcgtg gttgtcgttt ggttattctg tgaagcagcc aagccaggct attgttatga
1681 aaatttgtcg tctgtaagca tgtgaacttc cgatgttgcc acatgctgga tcagtctgaa
1741 taagtaagta tgcagctcta ggtggtcagc tgcgtctacc acaatgagca tgaacgtatg
1801 gagaaatatc tgtgaacccc atttggttta tgaataagat ttgttttcc cgagttaaaa
1861 aaaaaaaaaa aaa
```

Figure 4

NUCLEIC ACID DETECTION METHOD

CROSS-REFERENCE TO RELATED APPLICATIONS

This application claims benefit of U.S. Provisional Application Ser. No. 60/364,230, entitled "Nucleic Acid Detection Method," which was filed Mar. 13, 2002, the entire content of which is hereby incorporated by reference.

BACKGROUND OF THE INVENTION

This invention relates the field of molecular biology. More particularly, this invention relates to detection and quantitation of a particular nucleic acid molecule in a sample.

Various methods are known for detecting the presence of a particular nucleic acid molecule in a sample. These methods include the polymerase chain reaction (PCR), ligase chain reaction (LCR), nucleic acid sequence based amplification, strand displacement amplification, and amplification with Qo replicase (see, e.g., U.S. Pat. No. 4,683,195; Birkenmeye and Mushahwar, *J. Virol. Method* 35: 117-126, 1991; Landegren, *Trends Genetics* 9: 199-202, 1993).

However, all of the above-methods are mistake-prone due to the numerous amplifications of the nucleic acid molecule. In addition, because sequence-specific oligonucleotides and primers must be produced for each particular nucleic acid molecule to be detected, the above-methods are very costly.

Thus, there remains a need to identify a rapid, reliable, and cost-effective method for detecting a particular nucleic acid molecule in a sample.

SUMMARY OF THE INVENTION

The invention provides rapid, reliable, and cost-effective methods for detecting a particular nucleic acid molecule in a sample. Using the methods of the invention, the presence of a nucleic acid molecule having a known sequence can be detected from among a large number of molecules.

Accordingly, in one aspect, the invention provides a method for detecting the presence of a target nucleic acid molecule in a plurality of templates. The method includes (a) combining: (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence of the detection probe; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide that is not complementary to the second portion of the known nucleotide sequence of the target nucleic acid molecule; and (v) a plurality of templates suspected of containing the target nucleic acid molecule; wherein the combining is under conditions wherein complementary sequences hybridize to one another; (b) incubating the product of step (a) with a ligase under conditions wherein the ligase forms a covalent bond between the 3' terminus of the first oligonucleotide (which is hybridized to first portion of the known nucleotide sequence) and the 5' terminus of the second oligonucleotide (which is hybridized to the second portion of the known nucleotide sequence); (c) incubating the product of step (b) with a DNA polymerase under conditions wherein the primer is extended; and (d) detecting the presence of a non-hybridized detection probe, wherein the presence of the non-hybridized detection probe indicates the presence of the target nucleic acid molecule in the plurality of templates. In some embodiments, the non-hybridized detection probe is shortened.

In another aspect, the invention provides a method for detecting the presence of a target nucleic acid molecule in a plurality of templates, comprising: (a) combining: (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence of the detection probe; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide that is not complementary to the second portion of the known nucleotide sequence of the target nucleic acid molecule; and (v) a plurality of templates suspected of containing the target nucleic acid molecule; wherein the combining is under conditions where complementary sequences hybridize to one another; (b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence; (c) incubating the product of step (b) with a DNA polymerase and a second primer comprising a 3' terminal sequence that is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence) under conditions wherein the target nucleic acid molecule is amplified by extension of the primer and second primer; (d) detecting the presence of a non-hybridized detection probe, wherein the presence of the non-hybridized detection probe indicates the presence of the target nucleic acid molecule in the plurality of templates. In some embodiments, the non-hybridized detection probe is shortened. In certain embodiments, the nucleotide sequence of the primer and the second primer is the same. In some embodiments, the 3' terminal sequence of the second primer is about twenty nucleotides in length.

In another aspect, the invention provides a method for detecting the presence of a target nucleic acid molecule in a plurality of templates, comprising: (a) combining: (i) a detection probe comprising a universal sequence; (ii) a first oligonucleotide comprising a 3' terminal sequence that is complementary to a first portion of a known nucleotide sequence of a target nucleic acid molecule and a second sequence that is complementary to the universal sequence of the detection probe; (iii) a second oligonucleotide comprising a 5' terminal sequence that is complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another; (b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence; (c) incubating the product of step (b) with a DNA polymerase and a primer comprising a 3' terminal sequence that is complementary to a portion of the second oligonucleotide that is not complementary to the second portion of the known nucleotide sequence of the target nucleic acid molecule under conditions wherein the primer is extended; and (d) detecting the presence of a non-hybridized detection probe, wherein the presence of the non-hybridized detection probe indicates the presence of the target nucleic acid molecule in the plurality of templates. In some embodiments, the non-hybridized detection probe is shortened.

In yet another aspect, the invention provides a method for detecting the presence of a target nucleic acid molecule in a plurality of templates, comprising: (a) combining: (i) a detection probe comprising a universal sequence; (ii) a first oligonucleotide comprising a 3' terminal sequence that is complementary to a first portion of a known nucleotide sequence of a target nucleic acid molecule and a second sequence that is complementary to the universal sequence of the detection probe; (iii) a second oligonucleotide comprising a 5' terminal sequence that is complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another; (b) incubating the product of step (a) with a ligase under conditions wherein the ligase forms a covalent bond between the 3' terminus of the first oligonucleotide (that is hybridized to first portion of the known nucleotide sequence) and the 5' terminus of the second oligonucleotide (that is hybridized to the second portion of the known nucleotide sequence); (c) incubating the product of step (b) with a DNA polymerase, a primer comprising a 3' terminal sequence complementary to a portion of the second oligonucleotide that is not complementary to the second portion of the known nucleotide sequence of the target nucleic acid molecule, and a second primer comprising a 3' terminal sequence that is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence) under conditions wherein the target nucleic acid molecule is amplified by extension of the primer and second primer; and (d) detecting the presence of a non-hybridized detection probe, wherein the presence of the non-hybridized detection probe indicates the presence of the target nucleic acid molecule in the plurality of templates. In some embodiments, the non-hybridized detection probe is shortened. In certain embodiments, the nucleotide sequence of the primer and the second primer is the same. In some embodiments, the 3' terminal sequence of the second primer is about twenty nucleotides in length.

In yet another aspect, the invention provides a method for detecting the presence of a target nucleic acid molecule in a plurality of templates, comprising: (a) combining (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another; (b) incubating the product of step (a) with a detection probe comprising the universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence; (c) incubating the product of step (b) with a DNA polymerase and a primer comprising a 3' terminal sequence complementary to the 3' sequence of the second oligonucleotide under conditions wherein the primer is extended; and (d) detecting the presence of a non-hybridized detection probe, wherein the presence of the non-hybridized detection probe indicates the presence of the target nucleic acid molecule in the plurality of templates. In some embodiments, the non-hybridized detection probe is shortened.

In another aspect, the invention provides a method for detecting the presence of a target nucleic acid molecule in a plurality of templates, comprising: (a) combining: (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another; (b) incubating the product of step (a) with a detection probe comprising the universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence; (c) incubating the product of step (b) with a DNA polymerase, a primer comprising a 3' terminal sequence complementary to a portion of the second oligonucleotide that is not complementary to the second portion of the known nucleotide sequence of the target nucleic acid molecule, and a second primer comprising a 3' terminal sequence that is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence) under conditions wherein the target nucleic acid molecule is amplified by extension of the primer and second primer; and (d) detecting the presence of a non-hybridized detection probe, wherein the presence of the non-hybridized detection probe indicates the presence of the target nucleic acid molecule in the plurality of templates. In some embodiments, the non-hybridized detection probe is shortened. In certain embodiments, the nucleotide sequence of the primer and the second primer is the same. In some embodiments, the 3' terminal sequence of the second primer is about twenty nucleotides in length.

In various embodiments of the above-aspects of the invention, the detection probe is labeled. In particular embodiments, the detection probe is fluorescently labeled, labeled with a reporter dye, radiolabeled (e.g., with $^{32}P$, $^{35}S$, or $^{3}H$), and/or labeled by other means (e.g., biotinylated). In certain embodiments, the 3' terminus of the detection probe is labeled. In some embodiments, the 5' terminus of the detection probe is covalently bonded to a quenching moiety.

In certain embodiments, the 5' terminus of the second oligonucleotide is phosphorylated.

In particular embodiments of the above-aspects, the 3' terminal sequence of the first oligonucleotide complementary to the first portion of the known nucleotide sequence of the target nucleic acid molecule is about twenty nucleotides in length. In certain embodiments, the 3' terminal sequence of the second oligonucleotide complementary to the second portion of the known nucleotide sequence of the target nucleic acid molecule is about twenty nucleotides in length.

In some embodiments of the above-aspects of the invention, the universal sequence is about twenty nucleotides in length. In certain embodiments, the first oligonucleotide is about sixty nucleotides in length. In some embodiments, the second oligonucleotide is about forty nucleotides in length. In particular embodiments, the 3' terminal sequence of the primer is about twenty nucleotides in length.

In another aspect, the invention provides a kit for detecting the presence of a target nucleic acid molecule in a plurality of templates, comprising: (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence of the detection probe; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide that is not complementary to the second portion of the known nucleotide sequence of the target nucleic acid molecule; and (v) means for detecting non-hybridized detection probe. In some embodiments, the non-hybridized detection probe is shortened.

In certain embodiments, the second sequence of the first oligonucleotide is in the middle of the first oligonucleotide. In certain embodiments, the 3' terminal sequence of the primer that is complementary to the 3' sequence of the second oligonucleotide.

In certain embodiments of this aspect of the invention, the kit further comprises a ligase. In some embodiments, the kit further comprises a DNA polymerase. In particular embodiments, the kit further comprises a second primer comprising a 3' terminal sequence that is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence). In certain embodiments, the 5' terminal sequence of the first oligonucleotide of the kit is complementary to the 3' sequence of the second oligonucleotide.

BRIEF DESCRIPTION OF THE DRAWINGS

FIG. 1A shows the combination of the target nucleic acid molecule, the first oligonucleotide (whose 3'terminal sequence is complementary to the 3' portion of the target nucleic acid molecule), the second oligonucleotide (whose 5' terminal sequence is complementary to the 5' portion of the target nucleic acid molecule), the detection probe (comprising a universal sequence complementary to the second sequence of the first oligonucleotide), and the primer (whose 3' terminal sequence is complementary to the 3' sequence of the second oligonucleotide. If the target nucleic acid molecule is present in the plurality of templates, the first and second oligonucleotide hybridize to adjacent portions of the target nucleic acid molecule, as shown in FIG. 1B. If the 5' and 3' portions of the nucleic acid molecule are adjacent, addition of ligase creates a covalent bond (depicted as a black triangle) between the 5' terminal sequence of the second oligonucleotide and the 3' terminal sequence of the first oligonucleotide, as shown in FIG. 1C. FIG. 1D shows the displacement of the detection probe from the first oligonucleotide by the DNA polymerase as it extends the primer.

FIG. 2A shows the combination of the target nucleic acid molecule, the first oligonucleotide (whose 3'terminal sequence is complementary to the 3' portion of the target nucleic acid molecule), the second oligonucleotide (whose 5' terminal sequence is complementary to the 5' portion of the target nucleic acid molecule), the detection probe (comprising a universal sequence complementary to the second sequence of the first oligonucleotide), the primer (whose 3' terminal sequence is complementary to the 3' sequence of the second oligonucleotide, and the second primer (whose 3' terminal sequence is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence of the detection probe)). In FIG. 2B, if the target nucleic acid molecule is present in the plurality of templates, the first and second oligonucleotide hybridize to adjacent portions of the target nucleic acid molecule. In FIG. 2C, if the 5' and 3' portions of the nucleic acid molecule are adjacent, addition of ligase creates a covalent bond (depicted as a black triangle) between the 5' terminal sequence of the second oligonucleotide and the 3' terminal sequence of the first oligonucleotide. FIG. 2D shows the repeated displacement of the detection probe from the first oligonucleotide by the DNA polymerase as it extends the primer, first using the ligated first and second oligonucleotide as a template, and then using as a template the nucleic acid molecule created by extension of the second primer.

FIG. 3 is a schematic representation of the mRNA sequence of *Z. mays* mRNA encoding for NAD(P)H:Nitrate reductase (SEQ ID NO:3).

FIG. 4 is a schematic representation of the mRNA sequence of *Z. mays* mRNA encoding for fertilization-S-adenosylmethionine decarboxylase (SEQ ID NO:10).

DETAILED DESCRIPTION

Figure 1A:
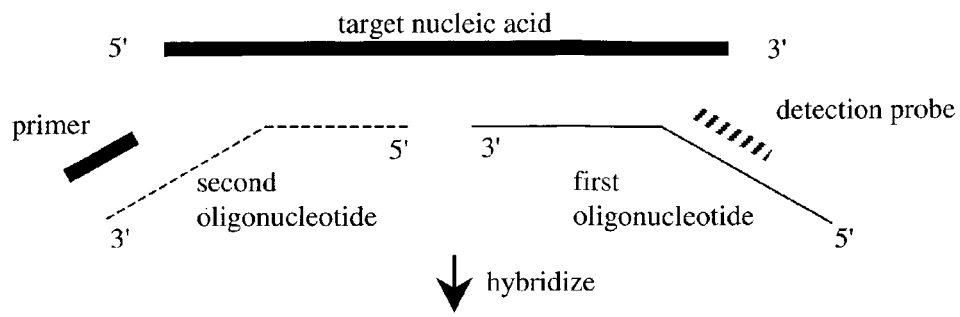
FIGS. 1A-1D are a series of schematic representations showing one non-limiting method of the invention.
Figure 1B:
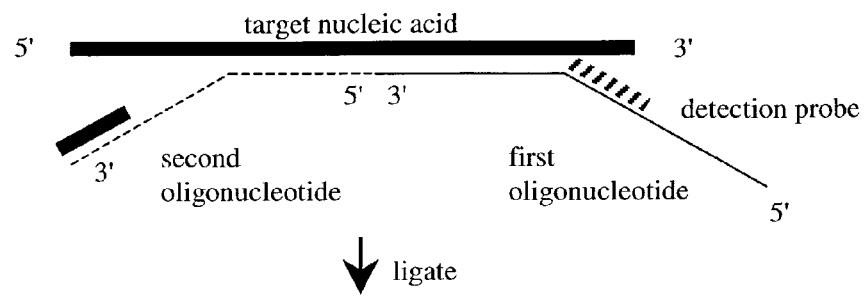

The patent and scientific literature referred to herein establishes knowledge that is available to those with skill in the art. The issued U.S. patents, allowed applications, published foreign applications, and references, including GenBank database sequences, that are cited herein are hereby incorporated by reference to the same extent as if each was specifically and individually indicated to be incorporated by reference.

The present invention stems from the discovery of a straightforward method to rapidly and reliably detect the presence, in a sample, of a target nucleic acid molecule having a known nucleic acid sequence. The present invention allows the rapid and reliable detection, in a sample, of the presence of a target nucleic acid molecule having a known nucleic acid sequence. In some embodiments, the methods of the invention do not use the polymerase chain reaction (see FIGS. 1A-1D). In other embodiments of the invention, the polymerase chain reaction is used to amplify the signal of the detection probe (see FIGS. 2A-2D). Thus, the invention provides a very straightforward method for detecting the presence of such a target nucleic acid molecule that employs oligonucleotides that specifically hybridize to the known sequence, a DNA polymerase, a reporter probe, and a DNA ligase.

Accordingly, the invention provides a method for detecting the presence of a target nucleic acid molecule in a plurality of templates.

As used herein, by "nucleic acid molecule" is meant a single-stranded molecule comprising nucleotides, wherein the nucleotides are deoxyribonucleic acid (DNA) nucleotides or ribonucleic acid (RNA) nucleotides. A nucleic acid molecule of the invention may be of any length (i.e., may comprise any number of nucleotides). Since complementary nucleotides on two single stranded nucleic acid molecules hybridize to one another, the term, "nucleic acid molecule" also includes double-stranded molecules which can be "melted" to produce two complementary single-stranded nucleic acid molecules (see, e.g., Ausubel et al., *Current Protocols in Molecular Biology*, John Wiley & Sons, New York, N.Y., 1994).

The term, "plurality of templates," means a sample of nucleic acid molecules which may include other molecules, such as proteins or carbohydrates. Thus, a plurality of templates includes, without limitation, a sample of the total genome of an organism, a cDNA or DNA library, or a sample of the total RNA (or mRNA) from an organism. As contemplated in the present invention, an "organism" includes prokaryotes, viruses, as well as lower and higher eukaryotes, such as plants (both Dicotyledones and Monocotyledones) and animals (e.g., humans, rodents, non-human primates, avians, and domesticated mammals).

In the first step of the methods of the invention, the following are combined under conditions wherein complementary sequences hybridize to one another: (i) a first oligonucleotide comprising a 3' terminal sequence complementary to a first portion of a known nucleotide sequence of a target nucleic acid molecule and a second sequence (i.e., 5' to the 3' terminal sequence) that is complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule.

In a variation of the first step, the combination also includes a detection probe comprising a universal sequence. In a variation of the first step, also included in the combination is a primer comprising a 3' terminal sequence complementary to a portion of the second oligonucleotide that is not complementary to the second portion of the known nucleotide sequence of the target nucleic acid molecule (e.g., the 3' terminal sequence of the primer is complementary to the 3' terminal sequence of the second oligonucleotide).

For purposes of the invention, the term "complementary" means having the ability to hybridize to a genomic region, a gene, cDNA, or an RNA transcript thereof as the result of base-specific hydrogen bonding between complementary strands to form Watson-Crick or Hoogstein base pairs. As used herein, "hybridize" refers to the formation of a base-paired interaction between single-stranded nucleic acid molecules (see, e.g., Ausubel et al., supra).

The exact fraction of the nucleotides which must be complementary in order to obtain stable hybridization varies with a number of hybridization condition factors, including, without limitation, nucleotide sequence (e.g., G and C content of the shorter of the two single stranded nucleic acid molecules), the location of the mismatches along the two molecules, salt and/or formamide concentrations of the hybridization buffers and washing solutions, temperature, and pH (see, e.g., Ausubel et al., supra; Sambrook et al., *Molecular Cloning. A Laboratory Manual*, $2^{nd}$ Ed., Cold Spring Harbor Laboratory, Cold Spring Harbor, N.Y., 1989). Formulae for estimating the melting temperature ($T_M$) of a double-stranded nucleic acid molecule (i.e., the temperature at which the double-stranded molecule becomes single stranded) are known (see, e.g., Sambrook et al., supra, particularly at 9.51 and 11.46).

According to the invention, where nucleic acid molecules are combined "under conditions wherein complementary sequences hybridize to one another," then the hybridization conditions are such that two nucleotide sequences with an exact match for base pairing, or only a small percentage (1-10%) of base mismatch between the two sequences, form a base paired double-stranded nucleic acid molecule which is stable enough to allow detection. Thus, according to the invention, for two single-stranded nucleic acid molecules to hybridize to one another to form a double-stranded nucleic acid molecule, their nucleotide sequences form at least 90% base pairing of the nucleotides of the shorter of the two single-stranded nucleic acid molecules, or at least 95% base pairing, or at least 98% base pairing, or at least 99% base pairing, or form 100% base pairing of the nucleotides of the shorter of the two single-stranded nucleic acid molecules.

As used throughout, a "3' terminal sequence" and a "3' sequence" are both located in the 3' half of the indicated nucleic acid molecule; however, they differ in that the former is located at the 3' end of the indicated nucleic acid molecule while the latter may be located at the 3' end of the indicated nucleic acid molecule, but need not be. For example, a 3' sequence may be located in the 3' half of a nucleic acid molecule, and may or may not include the 3' terminal nucleotide. A "5' terminal sequence" similarly differs from a "5' sequence".

For purposes of the invention, "oligonucleotide," "probe," and "primer" are single-stranded nucleic acid molecules which can include polymers of two or more deoxyribonucleotides, ribonucleotides, or any combination thereof. Such oligonucleotides, probes, and primers of the invention can be from about 8 to about 80 nucleotides in length, from about 12 to about 50 nucleotides in length, or from about 15 to about 30 nucleotides in length. The nucleotides of an oligonucleotide, probe, or primer of the invention may be coupled to each other by any of the numerous known internucleotide linkages including, without limitation, phosphodiester, phosphotriester, phosphorothioate, or phosphoramidate linkages, or combinations thereof.

By "detection probe" is meant a nucleic acid molecule that is detectable. The detection probe may be detectable based upon its sequence, its length, or by its being labeled with a detectable moiety. For example, the probe may be labeled with a dye, may be labeled with a fluorophore, may be radiolabeled (e.g., with $^{32}P$, $^3H$, or $^{35}S$), or may be labeled by other means (e.g., biotinylated). In certain embodiments, the 3' terminus of the detection probe is covalently labeled to a reporter dye, such as a fluorophore. Note that where the detection probe is labeled with a detectable moiety, the detection probe need not be detectably labeled before being used in the first step of the method of the invention (i.e., the detection probe need not be detectably labeled when it is combined with the first oligonucleotide, second oligonucleotide, and plurality of templates suspected of containing a target nucleic acid molecule).

As used herein, by "universal sequence" is meant a sequence that is predetermined to hybridize to its complementary sequence under conditions wherein complementary sequences hybridize to one another. Some non-limiting criteria for a universal sequence include a high G+C content, the inability of the universal sequence to form a hairpin loop with itself, and the inability of the universal sequence to hybridize to a naturally-occurring nucleotide sequence in the plurality of templates. A universal sequence allows the use of the same detection probe to identify the presence of more than one target sequence. For example, if a universal sequence is used which is found not to hybridize to any naturally-occurring human sequences, then the same detection probe can be used to identify the presence of any human target sequence if the plurality of templates is composed of human nucleic acid molecules. In certain embodiments, the universal sequence is between about eleven to about twenty-five nucleotides in length. For example, the universal sequence is about twenty nucleotides in length.

The term, "second sequence," is used to mean a sequence that is located 5' to the 3' terminal sequence of the first oligonucleotide that is complementary to a first portion of a known nucleotide sequence of a target nucleic acid molecule. Thus, the second sequence may be in the middle of the first oligonucleotide, in the 5' half of the first oligonucleotide, or even in the 3' half of the first oligonucleotide, so long as the second sequence does not overlap with the 3' terminal sequence of the first oligonucleotide.

According to the invention, an "oligonucleotide" is a single-stranded nucleic acid molecule engineered such that a portion of the oligonucleotide hybridizes to a portion of the known sequence of a target nucleic acid molecule. By a "portion" of a nucleic acid molecule (e.g., an oligonucleotide or a known sequence of a target nucleic acid molecule) is meant anything less than the total nucleic acid molecule.

For example, if there is a 100 nucleotide-long known sequence in a target nucleic acid molecule, then a portion of the known sequence of the nucleic acid molecule includes fewer than 100 nucleotides.

The invention provides two oligonucleotides (namely a first oligonucleotide and a second oligonucleotide), each of which are designed to hybridize to adjacent portions of the known sequence of a target nucleic acid molecule. In accordance with the invention, the first oligonucleotide is designed such that its 3' terminal sequence is complementary to (and thus hybridizes to) a 3' portion of a known sequence of the target nucleic acid molecule. The second oligonucleotide is designed such that its 5' terminal sequence is complementary to (and thus hybridizes to) a 5' portion of a known sequence of the target nucleic acid molecule. As shown in FIGS. 1A, 1B, 2A, and 2B, in accordance with the invention, the nucleotide in the target nucleic acid molecule to which the 5' terminal nucleotide of the second oligonucleotide hybridizes is 5' adjacent to the nucleotide in the target nucleic acid molecule to which the 3' terminal nucleotide of the first oligonucleotide hybridizes.

In certain embodiments, the 3' terminal sequence of the first oligonucleotide which is complementary to the first portion (i.e., the 3' portion) of the known nucleotide sequence of the target nucleic acid molecule is between about fifteen to about fifty nucleotides in length. For example, the 3' terminal sequence of the first oligonucleotide is about twenty nucleotides in length. Similarly, the 5' terminal sequence of the second oligonucleotide which is complementary to the second portion (i.e., the 5' portion) of the known nucleotide sequence of the target nucleic acid molecule is between about fifteen to about fifty nucleotides in length. For example, the 5' terminal sequence of the second oligonucleotide is about twenty nucleotides in length.

In some embodiments of the invention, the first oligonucleotide is between about 25 to about 150 nucleotides in length. For example, the first oligonucleotide may be about 40 nucleotides in length, or about 60 nucleotides in length. In some embodiments, the second oligonucleotide is between about 25 to about 150 nucleotides in length. For example, the second oligonucleotide may be about 40 nucleotides in length, or about 40 nucleotides in length.

Figure 1C:
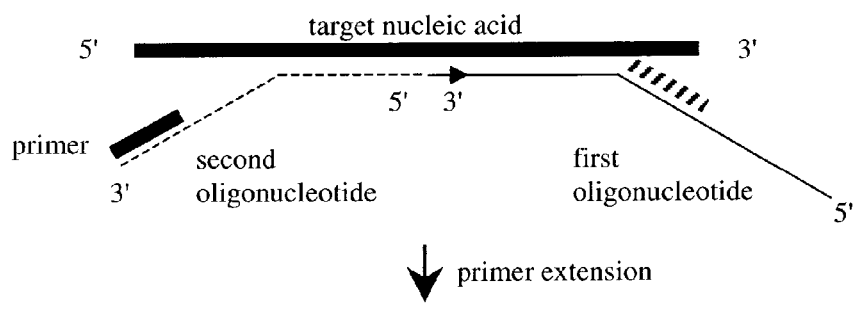
Figure 1D:
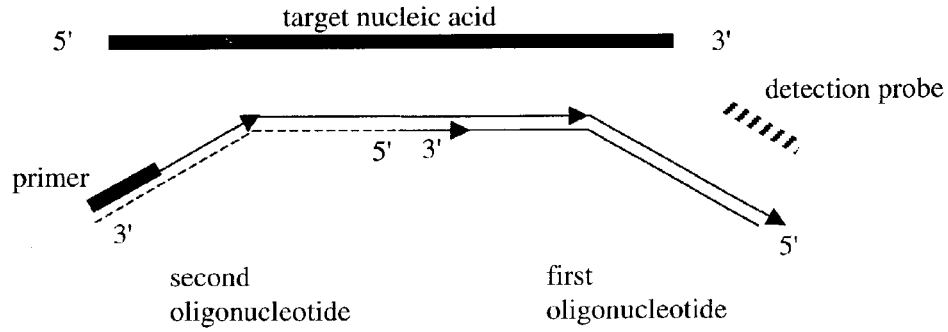
Figure 2A:
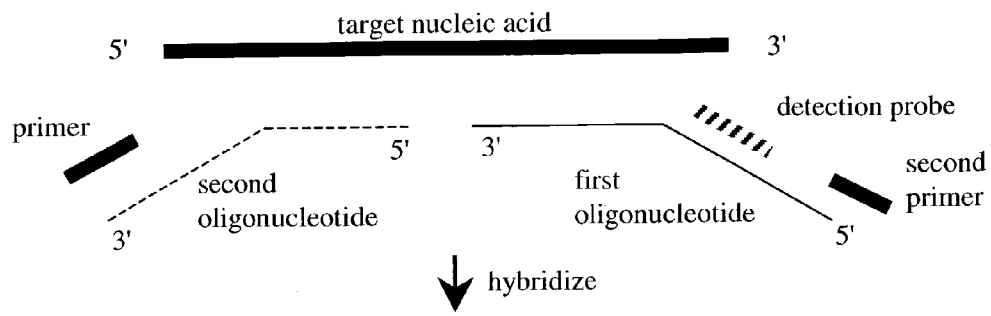
FIGS. 2A-2D are a series of schematic representations showing one non-limiting method of the invention.
Figure 2B:
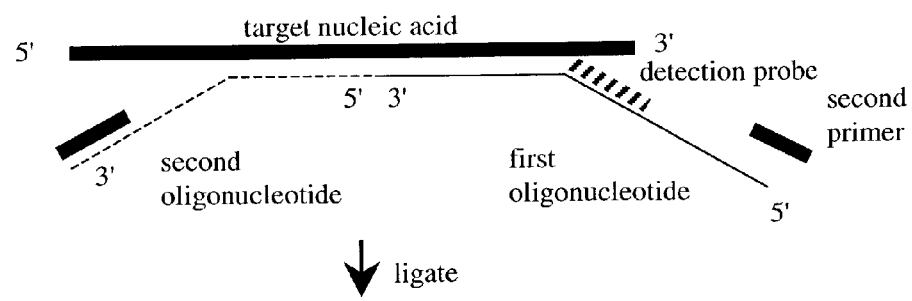
Figure 2C:
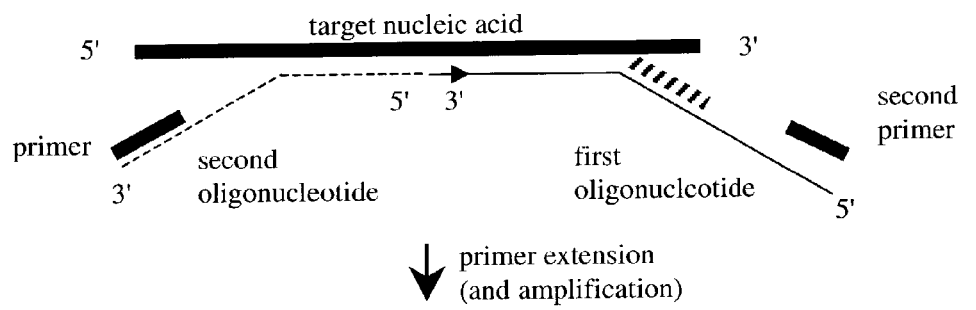

In the second step of the methods of the invention, the product of the first step of the methods of the invention is incubated with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence. A schematic of this ligation is shown in FIGS. 1C and 2C, where the covalent bond is depicted as a black arrow between the first and second oligonucleotides.

As used herein, a "ligase" is an enzyme that creates a covalent bond between a 5' terminus of a first nucleic acid molecule and a 3' terminus of a second nucleic acid molecule, where the 5' terminus of the first nucleic acid molecule and the 3' terminus of the second nucleic acid molecule are hybridized to adjacent nucleotides on a third nucleic acid molecule.

Thus, in accordance with the invention, a ligase covalently bonds the 5' terminus of the second oligonucleotide and the 3' terminus of the first oligonucleotide only if the nucleotides to which the 5' terminus of the second oligonucleotide and the 3' terminus of the first oligonucleotide hybridize are adjacent to one another in the target nucleic acid molecule. As used herein, by "adjacent" is meant that a two nucleotides on a target nucleic acid molecule are next to one another such that the 3' terminal nucleotide of a first oligonucleotide (which is hybridized to one of the two adjacent nucleotides of the target nucleic acid molecule) is ligatable to the 5' terminal nucleotide of a second oligonucleotide (which is hybridized to the second of the two adjacent nucleotides). Accordingly, no covalent bond is formed if there is an additional nucleotide at the juncture (i.e., an additional nucleotide of the target nucleic acid between the nucleotide to which the 5' terminus of the second oligonucleotide hybridizes and the nucleotides to which the 3' terminus of the first oligonucleotide hybridizes). Similarly, if there is a nucleotide missing at the juncture, such that either the 5' terminus of the second oligonucleotide or the 3' terminus of the first oligonucleotide is not hybridized to the target nucleic acid molecule, no covalent bond is formed by the ligase.

In certain embodiments of the invention, the 5' terminus of the second oligonucleotide is phosphorylated.

A ligase in accordance with the invention can be from any source. For example, T4 DNA ligase (from bacteriophage T4) may be employed (commercially available, for example, from New England Biolabs, Beverly, Mass.). Any ligase from any source may be employed in the methods of the invention including, without limitation, T7 DNA ligase (from bacteriophage T7), *E. coli* ligase, tRNA ligase, a ligase from yeast, a ligase from an insect cell, a ligase from a mammal (e.g., murine ligase), and human DNA ligase (e.g., human DNA ligase IV/XRCC4).

In the third step of the methods of the invention, the product of the second step of the method of the invention is incubated with a DNA polymerase under conditions wherein the primer is extended.

In certain embodiments, the 3' terminal sequence of the primer is between about 15 to about 50 nucleotides in length. For example, a primer of the invention may be about 10 nucleotides in length. As used herein, a "primer" is a nucleic acid molecule whose 3' terminus is hybridizable to a nucleotide on a complementary nucleic acid molecule such that, in the presence of DNA polymerase and appropriate free nucleotides (e.g., dATP, dGTP, dCTP, and dTTP), the primer is elongated by the DNA polymerase. The entire sequence of the primer may be hybridizable to a complementary nucleic acid molecule; however, this invention also encompasses those primers that are not fully hybridizable to a complementary nucleic acid molecule so long enough of the primer is hybridizable to allow the primer to be extended in the presence of DNA polymerase and free nucleotides. In certain embodiments, the sequence of the primer is selected such that it does not hybridize to any naturally-occurring nucleotide sequence in the plurality of templates. Thus, the primer can be used for the detection of more than one target nucleic acid molecule.

In the presence of a DNA polymerase, the primer is extended using the nucleic acid molecule to which the primer is hybridized as the template. Extension of the primer creates a new single-stranded nucleic acid molecule which is complementary to the single-stranded nucleic acid molecule to which the primer is hybridized. Thus, in accordance with the invention, where the primer hybridizes to the 3' sequence of the second oligonucleotide, the primer is extended until its 3' terminus reaches the 5' terminus of the second oligonucleotide. In some embodiments, the extension of the primer displaces the known sequence of the target nucleic acid molecule from the second oligonucleotide. If 5' terminus of the second oligonucleotide was covalently bonded by ligase to the 3' end of the first oligonucleotide (i.e., if the target nucleic acid molecule comprising the known nucleotide sequence was present in the plurality of templates), extension of the primer results in extension of the primer such that the 3' terminus of the extended primer is complementary to the 5' terminus of the first oligonucleotide. In reaching the second sequence of the first oligonucleotide, the DNA polymerase, in extending the primer, encounters the detection probe, thereby displacing it. Thus, the presence of a non-hybridized detection probe indicates the presence of the target nucleic acid molecule in the plurality of templates.

In some embodiments, a DNA polymerase used in the method of the invention has a 5' to 3' exonuclease activity (e.g, full length *E. coli* DNA polymerase I is useful in the methods of the invention). According to the invention, the DNA polymerase with 5' to 3' exonuclease activity degrades the 5' terminus of the detection probe. However, eventually there will be a sufficiently small number of nucleotides left in the detection probe that the detection probe will no longer hybridize to the first oligonucleotide and will fall off without being degraded by the oncoming DNA polymerase. Thus, in some embodiments of the methods of the invention, during the final step, the presence of a shortened non-hybridized detection probe is sought, wherein the presence of the shortened non-hybridized detection probe indicates the presence of the target nucleic acid molecule in the plurality of templates.

Because the detection probe is detectable, the means for detecting the detectable probe varies based upon how the detection probe was made detectable.

For example, in certain embodiments of the invention, the detection probe is made detectable using the fluorescence energy transfer (FRET) method (see, e.g., Mergny et al., *Nucl. Acids Res.* 22: 920-928, 1994). According to this embodiment, the detection probe is labeled with one fluorescent dye while the first oligonucleotide is labeled with a different fluorescent dye (e.g., at the 5' terminus of the first oligonucleotide). One of the two fluorescent dyes transfers energy to the other fluorescent dye such that the latter fluorescent dye emits fluorescence. Accordingly, only when the probe is hybridized to the first oligonucleotide does it emit fluorescence. Thus, non-hybridized detection probe is detectable because it does not emit fluorescence.

In certain embodiments of the invention, the 3' terminus of the detection probe is covalently labeled to a reporter dye and the 5' terminus of the detection probe is covalently labeled to a quenching moiety. Such reporter dyes and quenching moieties (and methods for covalently attaching them to a nucleic acid molecule) are known (see, e.g., Singer et al., U.S. Pat. No. 6,323,337; Tyagi and Kramer, *Nature Biotech.* 14: 303-308, 1996; Tyagi et al., *Nature Biotech.* 16: 49-53, 1998). As the oncoming DNA polymerase degrades the 5' terminus of the detection probe, it removes the quenching moiety. Thus, the non-hybridized detection probe retains the reporter dye which, in the absence of the quenching moiety, is no longer muted and so is readily detectable using standard methods.

In certain embodiments, where the DNA polymerase employed has a 5' to 3' exonuclease activity, and where the presence of the target nucleic acid molecule is indicated by the presence of a shortened non-hybridized detection probe, this shortened non-hybridized detection probe is detected by its length and the virtue that it is shorter than other non-hybridized detection probes. In a non-limiting example of this embodiment, an excess of detection probe is combined with the first oligonucleotide, the second oligonucleotide, the primer that hybridizes to the 3' sequence of the second oligonucleotide, and the plurality of templates suspected of containing the target nucleic acid. After ligation (with ligase) and primer extension (with DNA polymerase), if the target nucleic acid is present, the detection probe is shortened by the oncoming DNA polymerase with 5' to 3' exonuclease activity. However, because there is excess detection probe, some of the detection probe is never hybridized to the first oligonucleotide at all. To detect a shortened detection probe in this example, the nucleic acid molecules can be melted (e.g., by heating to 65° C. for 10 minutes) to render all of the nucleic acid molecules single stranded. Next, the single-stranded nucleic acid molecules can be resolved on a high density gel (e.g., a gel containing a high percentage or acrylamide or agarose). Because the primer is extended to at least the length of the second oligonucleotide (even if the target nucleic acid molecule was not present and the 5' terminus of the second oligonucleotide was not ligated to the 3' end of the first oligonucleotide), the shortest nucleic acid molecules will be the detection probe, and, if any, the shortened detection probe. If the detection probe was detectably labeled before being allowed to hybridize to the first oligonucleotide (e.g., if the detection probe was radiolabeled with $^{32}$P), then after resolving the single-stranded nucleic acid molecules on a high density gel (e.g., a 8% agarose gel), exposing the gel to X-ray film allows detection of not only the full length detection probe, but also the shortened detection probe (which, because of its length, migrates at a different band in the gel than the full length detection probe). Conversely, if the detection probe is not detectably labeled before being allowed to hybridize to the first oligonucleotide, after resolving the single-stranded nucleic acid molecules on a high density gel, to detect the shortened detection probe, the gel can be stained with ethidium bromide, and then examined under ultraviolet light. Based on the intensity of the ethidium bromide uptaken by the shortened non-hybridized detection probe, the number of copies of the target nucleic acid molecule in the plurality of templates is readily quantitated.

As used herein, a "DNA polymerase" is an enzyme which extends a primer by adding nucleotides, wherein the added nucleotides are complementary to the nucleic acid molecule to which the primer is hybridized. A DNA polymerase for use in the methods of the invention can be from any source. Non-limiting examples of DNA polymerase include *E. coli* DNA polymerase I, *E. coli* DNA polymerase II, and *E. coli* DNA polymerase III. In some embodiments, the DNA polymerase employed in the methods and kits of the invention has a 5' to 3' exonuclease activity. In certain embodiments, the DNA polymerase employed in the methods and kits of the invention has an associated helicase and/or gyrase activity.

Because the primer used in the methods of the invention may be designed to hybridize to a sequence that does not naturally occur in the plurality of templates, the methods of the invention can be used to simultaneously detect the presence of more than one target nucleic acid molecule in the same plurality of templates. For example, if the plurality of templates is a human cDNA library, and the two target nucleic acid molecules are insulin and human growth hormone, first and second oligonucleotides are generated for each target sequence. In addition, two detection probes are made which contain different universal sequences and which are labeled with different dyes. Of course, each of the second oligonucleotide for the insulin cDNA and the second oligonucleotide for the human growth hormone cDNA has a 3' sequence that is complementary to the primer. Thus, if insulin cDNA, but not human growth hormone cDNA, is present in the human cDNA library, then only one of the two dyes on the shortened detection probe is detected. If both insulin cDNA and human growth hormone cDNA are present, then both dyes from both shortened detection probes are detected. In addition, depending on the intensity of the dyes, a quantitation may be made to determine if more insulin cDNA is present than human growth hormone cDNA (or vice versa).

Figure 2D:
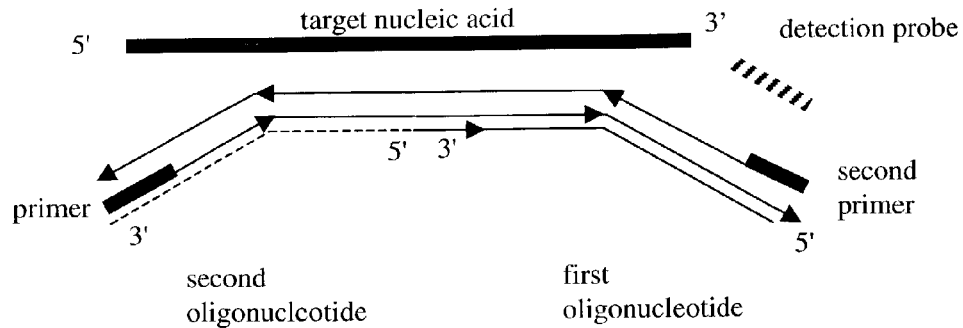

In a variation of the methods of the invention, a second primer is added in the third step. The 3' terminal sequence of the second primer is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence of the detection probe). In certain embodiments, the 3' terminal sequence of the second primer is between about 15 to about 50 nucleotides in length. For example, the 3' terminal sequence of the second primer is about 20 nucleotides in length. In certain embodiments, the portion of the primer that hybridizes to the second oligonucleotide and the portion of the second primer that is identical to the first oligonucleotide have the same sequence. Moreover, in certain embodiments, the primer and the second primer are identical (i.e., have identical sequences). In one example of this embodiment, the 5' sequence of the first oligonucleotide hybridizes to the 3' sequence of the second oligonucleotide.

Where a second primer is employed in the third step of the invention (regardless of whether the second primer is or is not identical to the primer), a thermostable DNA polymerase may be employed, and the method of the invention can be performed using the polymerase chain reaction (PCR), in which case the target nucleic acid molecule is amplified. Non-limiting examples of thermostable DNA polymerases include Taq DNA polymerase (from *Thermus aquaticus*), Pfu DNA polymerase (from *Pyrococcus furiosus*), and Vent DNA polymerase (from *Thermococcus litoralis*; also known as Tli DNA polymerase). In this embodiment of the invention, as shown in FIG. 2D, the detection probe, which, with each round of PCR hybridizes to the nucleotide sequence that was originally from the second sequence of the first oligonucleotide, is repeatedly shortened and displaced by the DNA polymerase as it extends the primer. In accordance with this embodiment of the invention, it may be desired to add detection probe prior to the last amplification round of the polymerase chain reaction, thus amplifying the signal given by the shortened non-hybridized detection probe if the target nucleic acid molecule was present in the plurality of templates and the ligation actually occurred.

For the method of the invention, the sequence of a portion of the nucleotide sequence of the target nucleic acid molecule must be known. For example, if the target nucleic acid molecule of interest encodes a protein (e.g., a plant calcium dependent protein kinase or human insulin), then the known nucleotide sequence can be either from the coding sequence (i.e., the sequences from the mRNA or exonic DNA that encodes amino acids) or from non-coding sequences (e.g., intronic DNA sequences or promoter/enhancer regions).

In one non-limiting example, where the target nucleic acid molecule is a protein, such as maize nitrate reductase (see, e.g., Chandok and Sopory, *J. Biol. Chem.* 273(30): 19235-19242, 1998), the plurality of templates is mRNA isolated from cells of the organism. Total mRNA is isolated according to standard methods (see, e.g., Ausubel et al., supra).

Using the known sequence of maize nitrate reductase (see, e.g., GenBank Accession No. AF153448; GenBank Accession No. X64446; Long et al., *Physiol. Plantarum* 85: 561-566, 1992), a first oligonucleotide and a second oligonucleotide can be designed and synthesized according to standard methods, whereby the 3' terminal sequence of the first oligonucleotide is complementary to a first portion of the maize nitrate reductase sequence and the 5' terminal sequence of the second oligonucleotide is complementary to a second portion of the maize nitrate reductase sequence. The 3' terminal nucleotide of the first oligonucleotide is complementary to a nucleotide of the maize nitrate reductase sequence that is directly adjacent to the nucleotide that is complementary to the 5' terminal nucleotide of the second oligonucleotide.

In one non-limiting embodiment, the method of the invention is useful for identifying the presence of a single nucleotide polymorphism (SNP) in a sample. SNPs are typically a single nucleotide change in the DNA of a organism's genetic material which may or may not result in an amino acid change in the organism's protein. Any given individual may have one or two alleles of a gene containing a particular SNP. A number of SNPs have been identified (see, e.g., Sachidanandam et al., *Nature* 409: 928-33, 2001).

In accordance with the methods of the invention, to determine whether or not an organism (e.g., a human) has a genome comprising an allele containing a particular SNP, oligonucleotides are designed whereby either the 5' terminal nucleotide of the second oligonucleotide or the 3' terminal nucleotide of the first oligonucleotide hybridizes to the SNP. Thus, if the target nucleic acid molecule (i.e., the gene) does not include the SNP, either the 5' terminal nucleotide of the second oligonucleotide or the 3' terminal nucleotide of the first oligonucleotide will not hybrize to the target nucleic acid molecule. Accordingly, the ligase will not ligate the 5' end of the second oligonucleotide to the 3' end of the first oligonucleotide. Note, however, that if the plurality of templates used is human genomic DNA, because there are two alleles of a given gene, there are three possible outcomes following the methods of the invention: no SNPs on either allele (in which case no shortened detection probe is created), the presence of SNPs on both alleles (in which case a large amount of shortened detection probe is created), or the presence of the SNP on one allele, but not the other allele (in which case a medium amount of shortened detection probe is created).

The use of the methods described herein to identify mutation in an expressed gene is also within the scope of the invention. Mutant forms of proteins such as ras p53, BRCA-1 and BRCA-2, RB1, and erbB are often associated with cancer (Dahiya and Deng, *Breast Cancer Research and Treatment* 52:185-200, 1998; Russo, A. et al., *Anticancer Research* 20:4841-4852, 2000; and Doolittle et al., *Exp. Mol. Pathol.* 70(3):289-301, 2001). In addition, mutant forms of proteins are also associated with other diseases. For example, mutant forms of prion proteins are found in humans affected by Creutzfeld-Jacob syndrome and livestock suffering from bovine spongiform encephalopathy and scrapie (see, e.g., Collinge, J., *Annual Review of Neuroscience* 24: 519-50, 2001). The mutated protein is mutated at one particular amino acid. For example, an oft-observed point mutation in human K-ras is at position 12, 13, or 61. By employing a first oligonucleotide whose 3' end or second oligonucleotide whose 5' end hybridizes to a nucleotide encoding the mutated amino acid, the methods of the invention can be used to quickly identify those human individuals having a point mutation in their K-ras protein.

The invention also provides a kit for detecting the presence of a target nucleic acid molecule in a plurality of templates. The kit of the invention includes the following: (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a primer comprising a 3' terminal sequence complementary to a portion of the second oligonucleotide that is not complementary to the second portion of the known nucleotide sequence of the target nucleic acid molecule. In some embodiments, the kit further comprises means for detecting the non-hybridized detection probe. Non-limiting examples of such means for detecting the shortened non-hybridized detection probe include a device to detect fluorescent emissions from the detection probe, a device to detect dye from the shorted detection probe, and a device to detect a shortened detection probe based on length.

In certain embodiments of the invention, the kit further comprises a ligase. In some embodiments, the kit further comprises a DNA polymerase. As described above, the DNA polymerase may be from any source, and, where the kit is used in a PCR reaction, the DNA polymerase may be from a thermostable organism. In some embodiments, the DNA polymerase has 5' to 3' exonuclease activity.

In particular embodiments, the kit further comprises a second primer, wherein the 3' terminal sequence of the second primer is identical to a portion of the first oligonucleotide that is 5' to both the 3' terminal sequence of the first oligonucleotide (that is complementary to the first portion of the known nucleotide sequence of the target nucleic acid molecule) and to the second sequence of the first oligonucleotide (that is complementary to the universal sequence). In some embodiments, the second primer comprises a 3' terminal sequence identical to the 5' terminal sequence of the first oligonucleotide. In certain embodiments, the 5' terminal sequence of the first oligonucleotide of the kit is complementary to the 3' sequence of the second oligonucleotide, thus enabling amplification of both strands (i.e., the initial first oligonucleotide ligated to the second oligonucleotide strand and the strand generated by extension of the primer) using the same primer (i.e., the primer that comprises a 3' terminal sequence complementary to the 3' sequence of the second oligonucleotide).

Thus, the present invention is based upon the high sensitivity of the ligation reaction, and can detect the presence of a single nucleotide change (e.g., can detect a SNP) or can detect different species of the same gene family. The method of the invention is cost effective because, for example, the detection probe (having the universal sequence) and the primer can be used for the detection of more than one target nucleic acid molecule. Moreover, the method of the invention does not require the synthesis of cDNA, thereby bypassing the time-consuming and costly process of covering mRNA into cDNA using reverse transcriptase.

In addition, given the diversity of different dyes available, more than one target nucleic acid molecule can be detected simultaneously from a single plurality of templates (see, e.g., Example II below).

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLE I

Detection of a Maize mRNA Encoding for NAD(P)H:Nitrate Reductase

To detect expression of an mRNA encoding for maize NAD(P)H:Nitrate reductase, total RNA from maize is isolated according to standard methods (see, e.g., Ausubel et al., supra).

First, a universal sequence is selected. In some embodiments, the universal sequence does not hybridize to a naturally-occurring maize RNA. The universal sequence used in this Example has the following nucleotide sequence:
5' CCCCCCCCCC CCCCCCCCCC 3' (SEQ ID NO:1)

Using SEQ ID NO:1, a detection probe is designed wherein the 5' end of the universal sequence is covalently linked to a TAMRA quenching moiety and the synthetic dye covalently linked to the 3' end of the universal sequence is the 6-FAM dye (see, e.g., Molecular Probes, *Handbook of Fluorescent Probes and Research Products*, Eighth Ed., 2001). The detection probe is labeled with the TAMRA and the 6-FAM moieties following known methods (see, e.g., Molecular Probes, supra; U.S. Pat. No. 6,323,337).

Next, the primer is designed. In some embodiments, the sequence of the primer does not hybridize to a naturally-occurring maize RNA. The primer used in this Example has the following nucleotide sequence:
5' CCAGGACCTGGTCGAGCT 3' (SEQ ID NO:2)

Next, oligonucleotides are designed based upon the maize NAD(P)H:Nitrate reductase mRNA sequence. Since RNA is used (and not first, for example, strand cDNA), the oligonucleotides are designed to be complementary to the mRNA strand. The nucleotide sequence for maize NAD(P)H:Nitrate reductase mRNA is known and is provided herein as FIG. 3 (SEQ ID NO:3; see also, e.g., GenBank Accession No. X64446; Long et al., *Physiol. Plantarum* 85: 561-566, 1992). (Note that in the sequence provided in FIG. 3, the uracil residues are replaced by thymidine residues. Thus, the sequence provided in FIG. 3 is actually the second strand cDNA of the maize NAD(P)H:Nitrate reductase mRNA sequence).

A first oligonucleotide and a second oligonucleotide are designed based upon nucleotides 61-100 of maize NAD(P)H:Nitrate reductase mRNA. The sequence is as follows:
5' aagctctgca tgcgcgcgta cacgcccacg agccccgtcg 3' (SEQ ID NO:4)

The first oligonucleotide is designed such that its 3' terminal twenty nucleotides are complementary to nucleotides 81-100 of the maize NAD(P)H:Nitrate reductase mRNA sequence (i.e., 5' cacgcccacg agccccgtcg 3' (SEQ ID NO:5). The second sequence of the first oligonucleotide is complementary to the universal sequence. The 5' terminal twenty nucleotides of the first oligonucleotide are simply random nucleotides, the sequence of which does not hybridize to a naturally-occurring maize RNA. Thus, a non-limiting first oligonucleotide of the invention has the following sequence:
5' gaattcggat ccaatgcctt gggggggggg gggggggggg cgacggggct cgtgggcgtg 3' (SEQ ID NO:6)

The second oligonucleotide is designed such that its 5' terminal twenty nucleotides are complementary to nucleotides 61-80 of the maize NAD(P)H:Nitrate reductase mRNA sequence (i.e., 5' aagctctgca tgcgcgcgta 3' (SEQ ID NO:7). The 3' terminal eighteen nucleotides of the second oligonucleotide are complementary to the primer. Thus, a non-limiting second oligonucleotide of the invention has the following sequence:
5' tacgcgcgca tgcagagctt agctcgacca ggtcctgg 3' (SEQ ID NO:8)

The oligonucleotides, primer, and detection probe are combined with the total maize RNA in a reaction tube (e.g., an Eppendorf microcentrifuge tube) and allowed to hybridize at room temperature. Next, T4 ligase is added to the reaction tube, and the tube is incubated overnight at 16° C. Next, the reaction tube is heated at 65° C. for ten minutes to deactivate the T4 ligase. The reaction tube contents may also be phenol:chloroform extracted and/or ethanol precipitated at this point to remove any T4 ligase. Next, DNA polymerase and an appropriate amount of dNTPs is added to the reaction tube, and the tube is incubated at 37° C. to allow the DNA polymerase to extend the primer.

At this point, if there is NAD(P)H:Nitrate reductase mRNA in the total maize RNA sample, the detection probe is shortened by the DNA polymerase, thereby removing the TAMRA quenching moiety from the 5' end of the detection probe. Therefore, the contents of the reaction tube are examined under a light that emits a wavelength that excites the 6-FAM fluorescent dye. The number of copies of NAD(P)H:Nitrate reductase mRNA present in the total maize mRNA sample is quantitated based upon the amount of fluorescence emitted by the FAM dye.

EXAMPLE II

Detection of Maize mRNAs Encoding for NAD(P)H:Nitrate Reductase and S-adenosylmethionine Decarboxylase in Maize Total RNA To simultaneously detect the presence of an mRNA encoding for NAD(P)H:Nitrate reductase and an mRNA encoding for S-adenosylmethionine decarboxylase in maize total RNA, total RNA from maize is isolated as described in Example I. In addition, the following molecules are synthesized:

1. A second detection probe (for S-adenosylmethionine decarboxylase mRNA) having a second universal sequence. The second universal sequence has the sequence:
5' GGAGGAGGAG GAGGAGGAGA 3' (SEQ ID NO:9).

Using SEQ ID NO:9, a second detection probe is designed wherein the 5' end of the second universal sequence is covalently linked to a TAMRA quenching moiety and the synthetic dye covalently linked to the 3' end of the universal sequence is the Tet dye, which emits light at a different wavelength than the FAM dye used on the first detection probe.

Next, oligonucleotides are designed based upon the S-adenosylmethionine decarboxylase mRNA sequence. Since RNA is used (and not first, for example, strand cDNA), the oligonucleotides are designed to be complementary to the mRNA strand. The nucleotide sequence for maize S-adenosylmethionine decarboxylase mRNA is known and is provided herein as FIG. 4 (SEQ ID NO:10; see also, e.g., GenBank Accession No. Y07767; Franceschetti et al., *Biochem. J.* 353 (Pt 2): 403-409, 2001). (Note that in the sequence provided in FIG. 4 is actually the second strand cDNA of the S-adenosylmethionine decarboxylase mRNA sequence).

A first oligonucleotide and a second oligonucleotide are designed based upon nucleotides 901-940 of maize S-adenosylmethionine decarboxylase mRNA. The sequence is as follows:

5' tacccagagc aaccaatggt taaccttgag atgtgcatga 3' (SEQ ID NO:11)

The first oligonucleotide is designed such that its 3' terminal twenty nucleotides are complementary to nucleotides 921-940 of the maize S-adenosylmethionine decarboxylase mRNA sequence (i.e., 5' taaccttgag atgtgcatga 3' (SEQ ID NO:12). The second sequence of the first oligonucleotide is complementary to the second universal sequence. The 5' terminal twenty nucleotides of the first oligonucleotide are simply random nucleotides, the sequence of which does not hybridize to a naturally-occurring maize RNA. Thus, a non-limiting first oligonucleotide of the invention has the following sequence:

5' tggaacacca gttcttgggc tctcctcctc ctcctcctcc tcatgcacat ctcaaggtta 3' (SEQ ID NO:13)

The second oligonucleotide is designed such that its 5' terminal twenty nucleotides are complementary to nucleotides 901-930 of the maize S-adenosylmethionine decarboxylase sequence (i.e., 5' tacccagagc aaccaatggt 3' (SEQ ID NO:14). The 3' terminal eighteen nucleotides of the second oligonucleotide are complementary to the primer (i.e., these 3' terminal eighteen nucleotides of the second oligonucleotide for S-adenosylmethionine decarboxylase mRNA are identical to the 3' terminal eighteen nucleotides of the second oligonucleotide for NAD(P)H:Nitrate reductase mRNA). Thus, a non-limiting second oligonucleotide of the invention has the following sequence:

5' accattggtt gctctgggta agctcgacca ggtcctgg 3' (SEQ ID NO:15)

The detection probes and the first and second oligonucleotides for both the S-adenosylmethionine decarboxylase mRNA and the NAD(P)H:Nitrate reductase mRNA, as well as primer (which is the same for both mRNAs) are combined with the total maize RNA in a reaction tube and allowed to hybridize at room temperature. Next, *E. coli* DNA ligase is added to the reaction tube, and the tube is incubated for approximately thirty minutes at 16° C. Next, the reaction tube is heated at 65° C. for ten minutes to deactivate the *E. coli* DNA ligase. Next, DNA polymerase and an appropriate amount of dNTPs is added to the reaction tube, and the tube is incubated at 37° C. to allow the DNA polymerase to extend the primer.

Next, the contents of the reaction tube are examined under a light that emits a wavelength that excites both the 6-FAM dye (for the NAD(P)H:Nitrate reductase mRNA) and the Tet dye (for the S-adenosylmethionine decarboxylase mRNA). If neither are present, neither dye is be seen. Similarly, if one is present, but not the other, that mRNA's dye is observed while the other dye is absent. If both mRNAs are present, both dyes are observed. In addition, the relative amounts of NAD(P)H:Nitrate reductase mRNA and S-adenosylmethionine decarboxylase mRNA can be quantitated (based upon the intensity of the dye), as well as compared to each other. For example, if there is more NAD(P)H:Nitrate reductase mRNA than S-adenosylmethionine decarboxylase mRNA in the total maize RNA sample, a greater quantity of 6-FAM dye is observed as compared to the quantity of Tet dye observed.

The invention claimed is:

1. A method for detecting the presence of a target nucleic acid molecule in a plurality of templates, comprising:
   (a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide, wherein the 3' terminal sequence of the primer is not complementary to the second portion of the known nucleotide sequence of the target nucleic acid molecule; and (v) a plurality of templates suspected of containing the target nucleic acid molecule, wherein the combining is under conditions wherein complementary sequences hybridize to one another;
   (b) incubating the product of step (a) with a ligase under conditions wherein the ligase forms a covalent bond between the 3' terminus of the first oligonucleotide hybridized to the first portion of the known nucleotide sequence and the 5' terminus of the second oligonucleotide hybridized to the second portion of the known nucleotide sequence;
   (c) incubating the product of step (b) with a DNA polymerase under conditions wherein the primer is extended; and
   (d) detecting the presence of a non-hybridized detection probe, wherein the non-hybridized detection probe is dissociated from the product of step (b) as a result of an activity of the DNA polymerase,
   wherein the presence of the non-hybridized detection probe indicates the presence of the target nucleic acid molecule in the plurality of templates.

2. A method for detecting the presence of a target nucleic acid molecule in a plurality of templates, comprising:
   (a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide, wherein the 3' terminal sequence of the primer is not complementary to the second portion of the known nucleotide sequence of the target nucleic acid molecule; and (v) a plurality of templates suspected of containing the target nucleic acid molecule: wherein the combining is under conditions wherein complementary sequences hybridize to one another;
   (b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;
   (c) incubating the product of step (b) with a DNA polymerase and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extension of the primer and second primer; and
   (d) detecting the presence of a non-hybridized detection probe, wherein the non-hybridized detection probe is dissociated from the product of step (b) as a result of an activity of the DNA polymerase,
   wherein the presence of the non-hybridized detection probe indicates the presence of the target nucleic acid molecule in the plurality of templates.

3. A method for detecting the presence of a target nucleic acid molecule in a plurality of templates, comprising:
   (a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another;

(b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;

(c) incubating the product of step (b) with a DNA polymerase and a primer comprising a 3' terminal sequence complementary to a portion of the second oligonucleotide, wherein the 3' terminal sequence of the primer is not complementary to the second portion of the known nucleotide sequence of the target nucleic acid molecule, under conditions wherein the primer is extended; and (d) detecting the presence of a non-hybridized detection probe, wherein the non-hybridized detection probe is dissociated from the product of step (b) as a result of an activity of the DNA polymerase, wherein the presence of the non-hybridized detection probe indicates the presence of the target nucleic acid molecule in the plurality of templates.

4. A method for detecting the presence of a target nucleic acid molecule in a plurality of templates, comprising:

(a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another;

(b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;

(c) incubating the product of step (b) with a DNA polymerase, a primer comprising a 3' terminal sequence complementary to a portion of the second oligonucleotide, wherein the 3' terminal sequence of the primer is not complementary to the second portion of the known nucleotide sequence of the target nucleic acid molecule, and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extension of the primer and second primer; and (d) detecting the presence of a non-hybridized detection probe, wherein the non-hybridized detection probe is dissociated from the product of step (b) as a result of an activity of the DNA polymerase, wherein the presence of the non-hybridized detection probe indicates the presence of the target nucleic acid molecule in the plurality of templates.

5. A method for detecting the presence of a target nucleic acid molecule in a plurality of templates, comprising:

(a) combining (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another;

(b) incubating the product of step (a) with a detection probe comprising a universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;

(c) incubating the product of step (b) with a DNA polymerase and a primer comprising a 3' terminal sequence complementary to a portion of the second oligonucleotide, wherein the 3' terminal sequence of the primer is not complementary to the second portion of the known nucleotide sequence of the target nucleic acid molecule, under conditions wherein the primer is extended; and (d) detecting the presence of a non-hybridized detection probe, wherein the non-hybridized detection probe is dissociated from the product of step (b) as a result of an activity of the DNA polymerase, wherein the presence of the non-hybridized detection probe indicates the presence of the target nucleic acid molecule in the plurality of templates.

6. A method for detecting the presence of a target nucleic acid molecule in a plurality of templates, comprising:

(a) combining (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another;

(b) incubating the product of step (a) with a detection probe comprising a universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;

(c) incubating the product of step (b) with a DNA polymerase, a primer comprising a 3' terminal sequence complementary to a portion of the second oligonucleotide, wherein the 3' terminal sequence is not complementary to the second portion of the known nucleotide sequence of the target nucleic acid molecule, and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extension of the primer and second primer; and (d) detecting the presence of a non-hybridized detection probe, wherein the non-hybridized detection probe is dissociated from the product of step (b) as a result of an activity of the DNA polymerase, wherein the presence of the non-hybridized detection probe indicates the presence of the target nucleic acid molecule in the plurality of templates.

7. The method of claims 2, 4, or 6, wherein the nucleotide sequence of the primer and the second primer is the same.

8. The method of claims 1, 2, 3, 4, 5, or 6, wherein the 3' terminus of the detection probe is labeled.

9. The method of claims 1, 2, 3, 4, 5, or 6, wherein the 5' terminus of the detection probe is covalently bonded to a quenching moiety.

10. The method of claims 1, 2, 3, 4, 5, or 6, wherein the 5' terminus of the second oligonucleotide is phosphorylated.

11. The method of claims 1, 2, 3, 4, 5, or 6, wherein the 3' terminal sequence of the first oligonucleotide complementary to the first portion of the known nucleotide sequence of the target nucleic acid molecule is about twenty nucleotides in length.

12. The method of claims 1, 2, 3, 4, 5, or 6, wherein the 5' terminal sequence of the second oligonucleotide complementary to the second portion of the known nucleotide sequence of the target nucleic acid molecule is about twenty nucleotides in length.

13. The method of claims 1, 2, 3, 4, 5, or 6, wherein the universal sequence is about twenty nucleotides in length.

14. The method of claims 1, 2, 3, 4, 5, or 6, wherein the first oligonucleotide is about sixty nucleotides in length.

15. The method of claims 1, 2, 3, 4, 5, or 6, wherein the second oligonucleotide is about forty nucleotides in length.

16. The method of claims 1, 2, 3, 4, 5, or 6, wherein the 3' terminal sequence of the primer is about twenty nucleotides in length.

17. The method of claims 2, 4, or 6, wherein the 3' terminal sequence of the second primer is about twenty nucleotides in length.

18. A method for detecting the presence of a target nucleic acid molecule in a plurality of templates, comprising:

(a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' therminal sequence complementary to a portion of the second oligonucleotide, wherein the 3' terminal sequence of the primer is not complementary to the second portion of the known nucleotide sequence of the target nucleic acid molecule; and (v) a plurality of templates suspected of containing the target nucleic acid molecule, wherein the combining is under conditions wherein complementary sequences hybridize to one another;

(b) incubating the product of step (a) with a ligase under conditions wherein the ligase forms a covalent bond between the 3' terminus of the first oligonucleotide hybridized to the first portion of the known nucleotide sequence and the 5' terminus of the second oligonucleotide hybridized to the second portion of the known nucleotide sequence;

(c) incubating the product of step (b) with a DNA polymerase having 5' to 3' exonuclease activity under conditions wherein the primer is extended; and (d) detecting the presence of a shortened non-hybridized detection probe, wherein the shortened non-hybridized detection probe dissociates from the product of step (b) as a result of an activity of the DNA polymerase, and further wherein the presence of the shortened non-hybridized detection probe indicates the presence of the target nucleic acid molecule in the plurality of templates.

19. A method for detecting the presence of a target nucleic acid molecule in a plurality of templates, comprising:

(a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; (iv) a primer comprising a 3' terminal sequence complementary to a portion of the second oligonucleotide, wherein the 3' terminal sequence of the primer is not complementary to the second portion of the known nucleotide sequence of the target nucleic acid molecule; and (v) a plurality of templates suspected of containing the target nucleic acid molecule: wherein the combining is under conditions wherein complementary sequences hybridize to one another;

(b) incubating the product of step (a) with a ligase under conditions wherein the ligase forum a covalent bond between the 3' terminus of the first oligonucleotide hybridized to first portion of the known nucleotide sequence and the 5' terminus of the second oligonucleotide hybridized to the second portion of the known nucleotide sequence;

(c) incubating the product of step (b) with a DNA polymerase having 5' to 3' exonuclease activity and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extension of the primer and second primer; and (d) detecting the presence of a shortened non-hybridized detection probe, wherein the shortened non-hybridized detection probe is dissociated from the product of step (b) as a result of an activity of the DNA polymerase, and further wherein the presence of the shortened non-hybridized detection probe indicates the presence of the target nucleic acid molecule in the plurality of templates.

20. A method for detecting the presence of a target nucleic acid molecule in a plurality of templates, comprising:
   (a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another;
   (b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;
   (c) incubating the product of step (b) with a DNA polymerase having 5' to 3' exonuclease activity and a primer comprising a 3' terminal sequence complementary to a portion of the second oligonucleotide, wherein the 3' terminal sequence of the primer is not complementary to the second portion of the known nucleotide sequence of the target nucleic acid molecule, under conditions wherein the primer is extended; and
   (d) detecting the presence of a shortened non-hybridized detection probe, wherein the shortened non-hybridized detection probe dissociates from the product of step (b) as a result of an activity of the DNA polymerase,
and further wherein the presence of the shortened non-hybridized detection probe indicates the presence of the target nucleic acid molecule in the plurality of templates.

21. A method for detecting the presence of a target nucleic acid molecule in a plurality of templates, comprising:
   (a) combining (i) a detection probe comprising a universal sequence; (ii) a first oligonucleotide comprising a 3' terminal sequence complementary to a first portion of a known nucleotide sequence of a target nucleic acid molecule and a second sequence complementary to the universal sequence; (iii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iv) a plurality of templates suspected of containing the target nucleic acid molecule; wherein the combining is under conditions wherein complementary sequences hybridize to one another;
   (b) incubating the product of step (a) with a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;
   (c) incubating the product of step (b) with a DNA polymerase having 5' to 3' exonuclease activity, a primer comprising a 3' terminal sequence complementary to a portion of the second oligonucleotide, wherein the 3' terminal sequence of the primer is not complementary to the second portion of the known nucleotide sequence of the target nucleic acid molecule, and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extension of the primer and second primer; and
   (d) detecting the presence of a shortened non-hybridized detection probe, wherein the shortened non-hybridized detection probe dissociates from the product of step (b) as a result of an activity of the DNA polymerase,
and further wherein the presence of the shortened non-hybridized detection probe indicates the presence of the target nucleic acid molecule in the plurality of templates.

22. A method for detecting the presence of a target nucleic acid molecule in a plurality of templates, comprising:
   (a) combining (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another;
   (b) incubating the product of step (a) with a detection probe comprising a universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;
   (c) incubating the product of step (b) with a DNA polymerase having 5' to 3' exonuclease activity and a primer comprising a 3' terminal sequence complementary to a portion of the second oligonucleotide, wherein the 3 terminal sequence of the primer is not complementary to the second portion of the known nucleotide sequence of the target nucleic acid molecule, under conditions wherein the primer is extended; and
   (d) detecting the presence of a shortened non-hybridized detection probe, wherein the shortened non-hybridized detection probe dissociates from the product of step (b) as a result of an activity of the DNA polymerase,
and further wherein the presence of the shortened non-hybridized detection probe indicates the presence of the target nucleic acid molecule in the plurality of templates.

23. A method for detecting the presence of a target nucleic acid molecule in a plurality of templates, comprising:
(a) combining (i) a first oligonucleotide comprising a 3' terminal sequence complementary to a first portion of a known nucleotide sequence of a target nucleic acid molecule and a second sequence complementary to a universal sequence; (ii) a second oligonucleotide comprising a 5' terminal sequence complementary to a second portion of the known nucleotide sequence of the target nucleic acid molecule, wherein the second portion of the known nucleotide sequence of the target nucleic acid molecule is adjacent to the first portion of the known nucleotide sequence; and (iii) a plurality of templates suspected of containing the target nucleic acid molecule; wherein the combining is under conditions wherein complementary sequences hybridize to one another;
(b) incubating the product of step (a) with a detection probe comprising a universal sequence under conditions where the detection probe hybridizes to the second sequence of the first oligonucleotide and a ligase under conditions wherein the ligase forms a covalent bond between the 3' terminus of the first oligonucleotide hybridized to first portion of the known nucleotide sequence and the 5' terminus of the second oligonucleotide hybridized to the second portion of the known nucleotide sequence;
(c) incubating the product of step (b) with a DNA polymerase having 5' to 3' exonuclease activity, a primer comprising a 3' terminal sequence complementary to a portion of the second oligonucleotide, wherein the 3' terminal sequence of the primer is not complementary to the second portion of the known nucleotide sequence of the target nucleic acid molecule, and a second primer, wherein the 3' terminal sequence of the second primer is identical to a portion of the first oligonucleotide that is 5' to both the 3' terminal sequence and the second sequence of the first oligonucleotide, under conditions wherein the target nucleic acid molecule is amplified by extepsion of the primer and second primer; and
(d) detecting the presence of a shortened non-hybridized detection probe, wherein the shortened non-hybridized detection probe is dissociated from the product of step (b) as a result of an activity of the DNA polymerase, and further wherein the presence of the shortened non-hybridized detection probe indicates the presence of the target nucleic acid molecule in the plurality of templates.

* * * * *

UNITED STATES PATENT AND TRADEMARK OFFICE
CERTIFICATE OF CORRECTION

| | |
|---|---|
| PATENT NO. | : 7,282,355 B2 |
| APPLICATION NO. | : 10/388329 |
| DATED | : October 16, 2007 |
| INVENTOR(S) | : Liang Shi |

It is certified that error appears in the above-identified patent and that said Letters Patent is hereby corrected as shown below:

Column 27, line 17, cancel the text beginning with "1. A method for detecting" to and ending "plurality of templates." in column 27, line 56, and insert the following claim:

1. A method for detecting the presence of a target nucleic acid molecule in a plurality of templates, the method comprising:
 (a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; (iv) a primer comprising a 3' terminal sequence, wherein the 3' terminal sequence of the primer is complementary to a portion of the second oligonucleotide, and further wherein the 3' terminal sequence of the primer is not complementary to the second portion of the known nucleotide sequence of the target nucleic acid molecule; and (v) a plurality of templates suspected of containing the target nucleic acid molecule, and forming a mixture;
 (b) adding a ligase to the mixture of step (a) and forming a reaction mixture, wherein, in the reaction mixture, a hybridization product comprising the detection probe, the first oligonucleotide, the second oligonucleotide, the primer, and the target nucleic acid molecule is formed and the ligase forms a covalent bond between the 3' terminus of the first oligonucleotide and the 5' terminus of the second oligonucleotide if the plurality of templates contains the target nucleic acid molecule;
 (c) adding a DNA polymerase to the reaction mixture of step (b) under conditions such that the detection probe is displaced from the first oligonucleotide by the DNA polymerase as it extends if the plurality of templates contains the target nucleic acid molecule; and
 (d) detecting the detection probe that is displaced from the first oligonucleotide, wherein the presence of the detection probe that is displaced from the first oligonucleotide indicates the presence of the target nucleic acid molecule in the plurality of templates.

Column 27, line 57, cancel the text beginning with "2. A method for detecting" to and ending "plurality of templates." in column 28, line 49, and insert the following claim:

UNITED STATES PATENT AND TRADEMARK OFFICE
CERTIFICATE OF CORRECTION

| | |
|---|---|
| PATENT NO. | : 7,282,355 B2 |
| APPLICATION NO. | : 10/388329 |
| DATED | : October 16, 2007 |
| INVENTOR(S) | : Liang Shi |

It is certified that error appears in the above-identified patent and that said Letters Patent is hereby corrected as shown below:

2. A method for detecting the presence of a target nucleic acid molecule in a plurality of templates, the method comprising:
    (a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; (iv) a first primer comprising a 3' terminal sequence, wherein the 3' terminal sequence of the primer is complementary to a portion of the second oligonucleotide, and further wherein the 3' terminal sequence of the first primer is not complementary to the second portion of the known nucleotide sequence of the target nucleic acid mulecule; and (v) a plurality of templates suspected of containing the target nucleic acid molecule, and forming a mixture;
    (b) adding a ligase to the mixture of step (a) and forming a reaction mixture, wherein, in the reaction mixture, a hybridization producing comprising the detection probe, the first oligonucleotide, the second oligonucleotide, the first primer, and the target nucleic acid molecule is formed, and further wherein the ligase forms a covalent bond between the 3' terminus of the first oligonucleotide and the 5' terminus of the second oligonucleotide if the plurality of templates contains the target nucleic acid molecule;
    (c) adding a DNA polymerase and a second primer to the reaction mixture of step (b), wherein the 3' terminal sequence of the second primer is identical to a portion of the first oligonucleotide that is 5' to both the 3' terminal sequence of the first oligonucleotide and the second sequence of the first oligonucleotide, under conditions such that the detection probe is displaced from the first oligonucleotide by the DNA polymerase and the target nucleic acid molecule is amplified by extension of the first primer and second primer if the plurality of templates contains the target nucleic acid molecule; and
    (d) detecting the detection probe that is displaced from the first oligonucleotide, wherein the presence of the detection probe that is displaced from the first oligonucleotide indicates the presence of the target nucleic acid molecule in the plurality of templates.

Column 28, line 50, cancel the text beginning with "3. A method for detecting" to and ending "plurality of templates." in column 29, line 22, and insert the following claim:

UNITED STATES PATENT AND TRADEMARK OFFICE
CERTIFICATE OF CORRECTION

| | | |
|---|---|---|
| PATENT NO. | : 7,282,355 B2 | |
| APPLICATION NO. | : 10/388329 | |
| DATED | : October 16, 2007 | |
| INVENTOR(S) | : Liang Shi | |

It is certified that error appears in the above-identified patent and that said Letters Patent is hereby corrected as shown below:

3. A method for detecting the presence of a target nucleic acid molecule in a plurality of templates, the method comprising:
(a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iv) a plurality of templates suspected of containing the target nucleic acid molecule, and forming a mixture;
(b) adding a ligase to the mixture of step (a) and forming a reaction mixture, wherein, in the reaction mixture, a hybridization product comprising the detection probe, the first oligonucleotide, the second oligonucleotide, and the target nucleic acid molecule is formed, and further wherein the ligase forms a covalent bond between the 3' terminus of the first oligonucleotide and the 5' terminus of the second oligonucleotide if the plurality of templates contains the target nucleic acid molecule;
(c) adding a DNA polymerase and a primer comprising a 3' terminal sequence, wherein the 3' terminal sequence of the primer is complementary to a portion of the second oligonucleotide and the 3' terminal sequence of the primer is not complementary to the second portion of the known nucleotide sequence of the target nucleic acid molecule, under conditions such that the detection probe is displaced from the first oligonucleotide by the DNA polymerase as it extends if the plurality of templates contains the target nucleic acid molecule; and
(d) detecting the detection probe that is displaced from the first oligonucleotide, wherein the presence of the detection probe that is displaced from the first oligonucleotide indicates the presence of the target nucleic acid molecule in the plurality of templates.

Column 29, line 23, cancel the text beginning with "4. A method for detecting" to and ending "plurality of templates." in column 29, line 67, and insert the following claim:

4. A method for detecting the presence of a target nucleic acid molecule in a plurality of templates, the method comprising:
(a) combining: (i) a detection probe comprising a universal sequence; (ii) a first oligonucleotide comprising a 3' terminal sequence and a second sequence complementary to the universal sequence, wherein the 3' terminal sequence of the first

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iv) a plurality of templates suspected of containing the target nucleic acid molecule, and forming a mixture;
    (b) adding a ligase to the mixture of step (a) and forming a reaction mixture, wherein, in the reaction mixture, a hybridization product comprising the detection probe, the first oligonucleotide, the second oligonucleotide, and the target nucleic acid molecule is formed and the ligase forms a covalent bond between the 3' terminus of the first oligonucleotide and the 5' terminus of the second oligonucleotide if the plurality of templates contains the target nucleic acid molecule;
    (c) adding a DNA polymerase, a first primer comprising a 3' terminal sequence, and a second primer, wherein the 3' terminal sequence of the first primer is complementary to a portion of the second oligonucleotide, the 3' terminal sequence of the first primer is not complementary to the second portion of the known nucleotide sequence of the target nucleic acid molecule, and the 3' terminal sequence of the second primer is identical to a portion of the first oligonucleotide that is 5' to both the 3' terminal sequence of the first oligonucleotide and the second sequence of the first oligonucleotide, under conditions such that the detection probe is displaced form the first oligonucleotide by the DNA polymerase and the target nucleic acid molecule is amplified by extension of the first primer and second primer if the plurality of templates contains the target nucleic acid molecule; and
    (d) detecting the detection probe that is displaced from the first oligonucleotide, wherein the presence of the detection probe that is displaced from the first oligonucleotide indicates the presence of the target nucleic acid molecule in the plurality of templates.

Column 30, line 1, cancel the text beginning with "5. A method for detecting" to and ending "plurality of templates." in column 30, line 42, and insert the following claim:

5. A method for detecting the presence of a target nucleic acid molecule in a plurality of templates, the method comprising:
    (a) combining: (i) a first oligonucleotide comprising a 3' terminal sequence and a second sequence complementary to a universal sequence, wherein the 3' terminal sequence of the first oligonucleotide is complementary to a first portion of a known nucleotide sequence of a target nucleic acid molecule; (ii) a second oligonucleotide comprising a 5' terminal sequence, wherein the 5' terminal sequence of the first

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iii) a plurality of templates suspected of containing the target nucleic acid molecule, and forming a mixture;

(b) adding a detection probe comprising the universal sequence and a ligase to the mixture of step (a) and forming a reaction mixture, wherein, in the reaction mixture, a hybridization product comprising the detection probe, the first oligonucleotide, the second oligonucleotide, and the target nucleic acid molecule is formed such that the detection probe hybridizes to the second sequence of the first oligonucleotide and the ligase forms a covalent bond between the 3' terminus of the first oligonucleotide and the 5' terminus of the second oligonucleotide if the plurality of templates contains the target nucleic acid molecule;

(c) adding a DNA polymerase and a primer comprising a 3' terminal sequence, wherein the 3' terminal sequence of the primer is complementary to a portion of the second oligonucleotide and the 3' terminal sequence of the primer is not complementary to the second portion of the known nucleotide sequence of the target nucleic acid molecule, under conditions such that the detection probe is displaced from the first oligonucleotide by the DNA polymerase as it extends if the plurality of templates contains the target nucleic acid molecule; and (d) detecting the detection probe that is displaced from the first oligonucleotide, wherein the presence of the detection probe that is displaced from the first oligonucleotide indicates the presence of the target nucleic acid molecule in the plurality of templates.

Column 30, line 43, cancel the text beginning with "6. A method for detecting" to and ending "plurality of templates." in column 31, line 22, and insert the following claim:

6. A method for detecting the presence of a target nucleic acid molecule in a plurality of templates, the method comprising:
(a) combining: (i) a first oligonucleotide comprising a 3' terminal sequence and a second sequence complementary to a universal sequence, wherein the 3' terminal sequence of the first oligonucleotide is complementary to a first portion of a known nucleotide sequence of a target nucleic acid molecule; (ii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iii) a plurality of templates suspected of containing

UNITED STATES PATENT AND TRADEMARK OFFICE
CERTIFICATE OF CORRECTION

| | |
|---|---|
| PATENT NO. | : 7,282,355 B2 |
| APPLICATION NO. | : 10/388329 |
| DATED | : October 16, 2007 |
| INVENTOR(S) | : Liang Shi |

It is certified that error appears in the above-identified patent and that said Letters Patent is hereby corrected as shown below:

the target nucleic acid molecule, and forming a mixture;

(b) adding a detection probe comprising the universal sequence and a ligase to the mixture of step (a) and forming a reaction mixture, wherein, in the reaction mixture, a hybridization product comprising the detection probe, the first oligonucleotide, the second oligonucleotide, and the target nucleic acid molecule is formed such that the detection probe hybridizes to the second sequence of the first oligonucleotide, and further wherein the ligase forms a covalent bond between the 3' terminus of the first oligonucleotide and the 5' terminus of the second oligonucleotide if the plurality of templates contains the target nucleic acid molecule;

(c) adding a DNA polymerase, a first primer comprising a 3' terminal sequence, and a second primer, wherein the 3' terminal sequence of the first primer is complementary to a portion of the second oligonucleotide and the 3' terminal sequence of the first primer is not complementary to the second portion of the known nucleotide sequence of the target nucleic acid molecule, and further wherein the 3' terminal sequence of the second primer is identical to a portion of the first oligonucleotide that is 5' to both the 3' terminal sequence of the first oligonucleotide and the second sequence of the first oligonucleotide, under conditions such that the detection probe is displaced from the first oligonucleotide by the DNA polymerase and the target nucleic acid molecule is amplified by extension of the first primer and second primer if the plurality of templates contains the target nucleic acid molecule; and (d) detecting the detection probe that is displaced from the first oligonucleotide, wherein the presence of the detection probe that is displaced from the first oligonucleotide indicates the presence of the target nucleic acid molecule in the plurality of templates.

Column 31, line 23, cancel the text beginning with "7. The method of claims 2, 4, or 6" to and ending "second primer is the same." in column 31, line 24, and insert the following claim:

7. The method of claims 2, 4, or 6, wherein the nucleotide sequence of the first primer and the second primer is the same.

Column 31, line 32, cancel the text beginning with "11. The method of claims 1, 2, 3, 4, 5, or 6" to and ending "twenty nucleotides in length." in column 31, line 36, and insert the following claim:

11. The method of claims 1, 2, 3, 4, 5, or 6, wherein the 3' terminal sequence of the first oligonucleotide that is complementary to the first portion of the known nucleotide sequence of the target nucleic acid molecule is about twenty nucleotides in length.

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

Column 31, line 37, cancel the text beginning with "12. The method of claims 1, 2, 3, 4, 5, or 6" to and ending "twenty nucleotides in length." in column 31, line 41, and insert the following claim:

12. The method of claims 1, 2, 3, 4, 5, or 6, wherein the 5' terminal sequence of the second oligonucleotide that is complementary to the second portion of the known nucleotide sequence of the target nucleic acid molecule is about twenty nucleotides in length.

Column 31, line 48, cancel the text beginning with "16. The method of claims 1,2, 3, 4, 5, or 6" to and ending "twenty nucleotides in length." in column 31, line 50, and insert the following claim:

16. The method of claims 1, 2, 3, 4, 5, or 6, wherein the 3' terminal sequence of the primer or the first primer is about twenty nucleotides in length.

Column 31, line 54, cancel the text beginning with "18. A method for detecting" to and ending "plurality of templates." in column 32, line 26, and insert the following claim:

18. A method for detecting the presence of a target nucleic acid molecule in a plurality of templates, the method comprising:
(a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; (iv) a primer comprising a 3' terminal sequence, wherein the 3' terminal sequence of the primer is complementary to a portion of the second oligonucleotide, and further wherein the 3' terminal sequence of the primer is not complementary to the second portion of the known nucleotide sequence of the target nucleic acid molecule; and (v) a plurality of templates suspected of containing the target nucleic acid molecule, and forming a mixture;
(b) adding a ligase to the mixture of step (a) and forming a reaction mixture, wherein, in the reaction mixture, a hybridization product comprising the detection probe, the first oligonucleotide, the second oligonucleotide, the primer, and the target

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

nucleic acid molecule is formed, and further wherein the ligase forms a covalent bond between the 3' terminus of the first oligonucleotide and the 5' terminus of the second oligonucleotide if the plurality of templates contains the target nucleic acid molecule;

(c) adding a DNA polymerase having 5' to 3' exonuclease activity to the reaction mixture of step (b) under conditions such that a shortened detection probe is released from the first oligonucleotide by the DNA polymerase as it extends if the plurality of templates contains the target nucleic acid molecule; and (d) detecting the shortened detection probe that is released from the first oligonucleotide, wherein the presence of the shortened detection probe that is released from the first oligonucleotide indicates the presence of the target nucleic acid molecule in the plurality of templates.

Column 32, line 27, cancel the text beginning with "19. A method for detecting" to and ending "plurality of templates." in column 33, line 5, and insert the following claim:

19. A method for detecting the presence of a target nucleic acid molecule in a plurality of templates, the method comprising:

(a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; (iv) a first primer comprising a 3' terminal sequence, wherein the 3' terminal sequence of the first primer is complementary to a portion of the second oligonucleotide, and further wherein the 3' terminal sequence of the primer is not complementary to the second portion of the known nucleotide sequence of the target nucleic acid molecule; and (v) a plurality of templates suspected of containing the target nucleic acid molecule, and forming a mixture;

(b) adding a ligase to the mixture of step (a) and forming a reaction mixture, wherein, in the reaction mixture, a hybridization product comprising the detection probe, the first oligonucleotide, the second oligonucleotide, the first primer, and the target nucleic acid molecule is formed, and further wherein the ligase forms a covalent bond between the 3' terminus of the first oligonucleotide and the 5' terminus of the second oligonucleotide if the plurality of templates contains the target nucleic acid molecule;

(c) adding a DNA polymerase having 5' to 3' exonuclease activity and a second

UNITED STATES PATENT AND TRADEMARK OFFICE
CERTIFICATE OF CORRECTION

PATENT NO.         : 7,282,355 B2
APPLICATION NO. : 10/388329
DATED                 : October 16, 2007
INVENTOR(S)       : Liang Shi It is certified that error appears in the above-identified patent and that said Letters Patent is hereby corrected as shown below:

primer to the reaction mixture of step (b), wherein the 3' terminal sequence of the second primer is identical to a portion of first the oligonucleotide that is 5' to both the 3' terminal sequence of the first oligonucleotide and the second sequence of the first oligonucleotide, under conditions such that a shortened detection probe is released from the first oligonucleotide by the DNA polymerase and the target nucleic acid molecule is amplified by extension of the first primer and second primer if the plurality of templates contains the target nucleic acid molecule; and (d) detecting the shortened detection probe that is released from the first oligonucleotide, wherein the presence of the shortened detection probe that is released from the first oligonucleotide indicates the presence of the target nucleic acid molecule in the plurality of templates.

Column 33, line 6, cancel the text beginning with "20. A method for detecting" to and ending "plurality of templates." in column 33, line 46, and insert the following claim:

20. A method for detecting the presence of a target nucleic acid molecule in a plurality of templates, the method comprising:

(a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iv) a plurality of templates suspected of containing the target nucleic acid molecule, and forming a mixture;

(b) adding a ligase to the mixture of step (a) and forming a reaction mixture, wherein, in the reaction mixture, a hybridization product comprising the detection probe, the first oligonucleotide, the second oligonucleotide, and the target nucleic acid molecule is formed, and further wherein the ligase forms a covalent bond between the 3' terminus of the first oligonucleotide and the 5' terminus of the second oligonucleotide if the plurality of templates contains the target nucleic acid molecule;

(c) adding a DNA polymerase having 5' to 3' exonuclease activity and a primer comprising a 3' terminal sequence, wherein the 3' terminal sequence of the primer is complementary to a portion of the second oligonucleotide and the 3' terminal sequence of the primer is not complementary to the second portion of the known nucleotide sequence of the target nucleic acid molecule, under conditions such that a shortened detection probe is released from the first oligonucleotide by the DNA polymerase as

UNITED STATES PATENT AND TRADEMARK OFFICE
CERTIFICATE OF CORRECTION

| | |
|---|---|
| PATENT NO. | : 7,282,355 B2 |
| APPLICATION NO. | : 10/388329 |
| DATED | : October 16, 2007 |
| INVENTOR(S) | : Liang Shi |

It is certified that error appears in the above-identified patent and that said Letters Patent is hereby corrected as shown below:

it extends if the plurality of templates contains the target nucleic acid molecule; and (d) detecting the shortened detection probe that is released from the first oligonucleotide, wherein the presence of the shortened detection probe that is released from the first oligonucleotide indicates the presence of the target nucleic acid molecule in the plurality of templates.

Column 33, line 46, cancel the text beginning with "21. A method for detecting" to and ending "plurality of templates." in column 34, line 24, and insert the following claim:

21. A method for detecting the presence of a target nucleic acid molecule in a plurality of templates, the method comprising:

(a) combining: (i) a detection probe comprising a universal sequence; (ii) a first oligonucleotide comprising a 3' terminal sequence and a second sequence complementary to the universal sequence, wherein the 3' terminal sequence of the first oligonucleotide is complementary to a first portion of a known nucleotide sequence of a target nucleic acid molecule; (iii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iv) a plurality of templates suspected of containing the target nucleic acid molecule, and forming a mixture;

(b) adding a ligase to the mixture of step (a) and forming a reaction mixture, wherein, in the reaction mixture, a hybridization product comprising the detection probe, the first oligonucleotide, the second oligonucleotide, and the target nucleic acid molecule is formed and the ligase forms a covalent bond between the 3' terminus of the first oligonucleotide and the 5' terminus of the second oligonucleotide if the plurality of templates contains the target nucleic acid molecule;

(c) adding a DNA polymerase having 5' to 3' exonuclease activity, a first primer comprising a 3' terminal sequence, and a second primer, wherein the 3' terminal sequence of the first primer is complementary to a portion of the second oligonucleotide and the 3' terminal sequence of the first primer is not complementary to the second portion of the known nucleotide sequence of the target nucleic acid molecule, and the 3' terminal sequence of the second primer is identical to a portion of the first oligonucleotide that is 5' to both the 3' terminal sequence of the first oligonucleotide and the second sequence of the first oligonucleotide, under conditions such that a shortened detection probe is released from the first oligonucleotide by the DNA polymerase and the target nucleic acid molecule is amplified by extension of the first primer and second primer if the plurality of templates contains the target nucleic acid molecule; and

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

(d) detecting the shortened detection probe that is released from the first oligonucleotide, wherein the presence of the shortened detection probe that is released from the first oligonucleotide indicates the presence of the target nucleic acid molecule in the plurality of templates.

Column 34, line 25, cancel the text beginning with "22. A method for detecting" to and ending "plurality of templates." in column 34, line 67, and insert the following claim:

22. A method for detecting the presence of a target nucleic acid molecule in a plurality of templates, the method comprising:
(a) combining: (i) a first oligonucleotide comprising a 3' terminal sequence and a second sequence complementary to a universal sequence, wherein the 3' terminal sequence of the first oligonucleotide is complementary to a first portion of a known nucleotide sequence of a target nucleic acid molecule; (ii) a second oligonucleotide comprising a 5' terminal sequence, wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iii) a plurality of templates suspected of containing the target nucleic acid molecule, and forming a mixture;
(b) adding a detection probe comprising the universal sequence and a ligase to the mixture of step (a) and forming a reaction mixture, wherein a hybridization product comprising the detection probe, the first oligonucleotide, the second oligonucleotide, and the target nucleic acid molecule is formed such that the detection probe hybridizes to the second sequence of the first oligonucleotide and the ligase forms a covalent bond between the 3' terminus of the first oligonucleotide and the 5' terminus of the second oligonucleotide if the plurality of templates contains the target nucleic acid molecule;
(c) adding a DNA polymerase having 5' to 3' exonuclease activity and a primer comprising a 3' terminal sequence wherein the 3' terminal sequence of the primer is complementary to a portion of the second oligonucleotide and the 3' terminal sequence of the primer is not complementary to the second portion of the known nucleotide sequence of the target nucleic acid molecule, under conditions so that a shortened detection probe is released from the first oligonucleotide by the DNA polymerase as it extends if the plurality of templates contains the target nucleic acid molecule; and
(d) detecting the shortened detection probe that is released from the first oligonucleotide, wherein the presence of the shortened detection probe that is released from the first oligonucleotide indicates the presence of the target nucleic acid molecule acid molecule in the plurality of templates.

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

Column 35, line 1, cancel the text beginning with "23. A method for detecting" to and ending "plurality of templates." in column 36, line 23, and insert the following claim:

23. A method for detecting the presence of a target nucleic acid molecule in a plurality of templates, the method comprising:
(a) combining: (i) a first oligonucleotide comprising a 3' terminal sequence and a second sequence complementary to a universal sequence, wherein the 3' terminal sequence of the first oligonucleotide is complementary to a first portion of a known sequence of a target nucleic acid molecule; (ii) a second oligonucleotide comprising a 5' terminal sequence wherein the 5' terminal sequence of the first oligonucleotide is complementary to a second portion of the known nucleotide sequence of the target nucleic acid molecule, and further wherein the second portion of the known nucleotide sequence of the target nucleic acid molecule is adjacent to the first portion of the known nucleotide sequence; and (iii) a plurality of templates suspected of containing the target nucleic acid molecule, and forming a mixture;
(b) adding a detection probe comprising the universal sequence and a ligase to the mixture of step (a) and forming a reaction mixture wherein, in the reaction mixture, a hybridization product comprising the detection probe, the first oligonucleotide, the second oligonucleotide, and the target nucleic acid molecule is formed such that the detection probe hybridizes to the second sequence of the first oligonucleotide and further wherein the ligase forms a covalent bond between the 3' terminus of the first oligonucleotide and the 5' terminus of the second oligonucleotide if the plurality of templates contains the target nucleic acid molecule;
(c) adding a DNA polymerase having 5' to 3' exonuclease activity, a first primer comprising a 3' terminal sequence and a second primer, wherein the 3' terminal sequence of the first primer is complementary to a portion of the second oligonucleotide, the 3' terminal sequence of the first primer is not complementary to the second portion of the known nucleotide sequence of the target nucleic acid molecule, and the 3' terminal sequence of the second primer is identical to a portion of the first oligonucleotide that is 5' to both the 3' terminal sequence of the first oligonucleotide and the second sequence of the first oligonucleotide, under conditions such that a shortened detection probe is released from the first oligonucleotide by the DNA polymerase and the target nucleic acid molecule is amplified by extension of the first primer and second primer if the plurality of templates contains the target nucleic acid molecule; and

UNITED STATES PATENT AND TRADEMARK OFFICE
CERTIFICATE OF CORRECTION

PATENT NO. : 7,282,355 B2
APPLICATION NO. : 10/388329
DATED : October 16, 2007
INVENTOR(S) : Liang Shi It is certified that error appears in the above-identified patent and that said Letters Patent is hereby corrected as shown below:

(d) detecting the shortened detection probe that is released from the first oligonucleotide, wherein the presence of the shortened detection probe that is released from the first oligonucleotide indicates the presence of the target nucleic acid molecule in the plurality of templates.

Signed and Sealed this

Twenty Second Day of April, 2008

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cccccccccc cccccccccc                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccaggacctg gtcgagct                                                      18

<210> SEQ ID NO 3
<211> LENGTH: 931
<212> TYPE: DNA
<213> ORGANISM: Zea mays
```

-continued

<400> SEQUENCE: 3

```
ccgcagaagc tcggccttcc cgtcggcagg cacgtgtacg tgtgcgcgtc gataggcggc      60
aagctctgca tgcgcgcgta cacgcccacg agccccgtcg acgaggtcgg ccacttcgat     120
ctcctcatca agatatactt caaggacgag daccccaagt accccaacgg cgggctcatg     180
tcgcagtacc tggactccct gccgctgggc gcgactattg acatcaaggg tccgcatagg     240
cacatcgagt acaccggccg ccgccgcttc gtggtgaacg gcaagcagcg tcacgcgcgc     300
aggctcgcca tgatccaggc cggcagaggg accacgcccg acgacgacac ggagcaggcc     360
gtgctgaggg accagcccga cgacgacacg gagatgcacc tcgtgtacgc gaaccgaacg     420
gaccacgaca tgctcctaag ggaggagatc gaccgcgctt ggctgccgcg cacccggcgc     480
ctcaaggtgt ggtacgtggt cagcaaggtc ccggaggacg ggtgggagta cggcgtgggg     540
agagtggacg agcatgtcat gagggagcac ctgcctctgg gagacagcga gaccattgcg     600
ctcgtgtgcg ggccgccggc gatgatcgag tgcacagtgc gcccgggcct ggagaagatg     660
gggtacgacc tcgacaaggc ttgtctcgtg ttctgagctc tgaatagcgg ctaacggatg     720
tcgtcaaggt gcaactgtac atagaaattc tgtggtgcct tgaatcttga accctagtaa     780
cgtgtcgatc tagctagaac tctaccgagt tctcttgtaa tactagcgat ttaaactggc     840
catggaagtt catactagct ggtgccatgg ccgtcttgtc aagatgagat gtattggtcc     900
tactatatac agcgcaataa aaaccccaag g                                    931
```

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
aagctctgca tgcgcgcgta cacgcccacg agccccgtcg                            40
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
cacgcccacg agccccgtcg                                                  20
```

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gaattcggat ccaatgcctt gggggggggg gggggggggg cgacggggct cgtgggcgtg      60
```

<210> SEQ ID NO 7
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 7
aagctctgca tgcgcgcgta                                                  20

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tacgcgcgca tgcagagctt agctcgacca ggtcctgg                              38

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggaggaggag gaggaggaga                                                  20

<210> SEQ ID NO 10
<211> LENGTH: 1873
<212> TYPE: DNA
<213> ORGANISM: Zea mays

<400> SEQUENCE: 10
acgaggtttc acacatagct tcgtcgattt gaatttgatg tactaatgga gtctaagggt      60
ggcaaaaagt ctagcagtag tcgttctatg atgtatgaag ctccccttgg ctacagcatt     120
gaggacgttc gacctgccgg aggcgtgaag aagttccagt ctgctgctta ctccaactgc     180
gcgaagaagc catcctgata tcccttttgg cttcctcatt ctagtagttt aggatttctt     240
ttctgacact ttgattctga ccaatctctc tggcctgctg cttcctgata atcgaccagt     300
tccccagtct tgctccttgc actcctccct ccatctccag cattgtgttc tgattcacct     360
gctccaatgg ctgttctttc tgctgctgat gcttccccgg tctcagctat cgggtttgag     420
ggctatgaga agcgccttga gatcacattc tctgaggcac ctgtctttgt ggaccctcat     480
gggcgtggtt tgcgtgccct ctccagggcc cagattgact ctgttctgga tcttgcacgg     540
tgcacaattg tgtctgagct ctccaacaag gatttcgact catatgtcct ttctgagtca     600
agcttgttta tctatcctct gaagattgtc atcaagacct gtggcactac caagctcctg     660
ctcaccattc aagaatcct tgagcttgct gaagagctgt ctatgccact tgctgctgtg      720
aagtactccc gtgggacgtt catctttcct ggcgcacagc cagcccccca caggagcttc     780
tctgaggaag ttgctgcact taaccgctac tttggcggcc tgaaatctgg tggtaatgct     840
tatgtgattg gagatccagc aagacctgga cagaagtggc acgtcttcta cgccactgag     900
tacccagagc aaccaatggt taaccttgag atgtgcatga ctggtctgga caagaagaaa     960
gcttgtgtct ttttcaagac taatgctgat gggaacacaa catgtgccaa ggaaatgaca    1020
aagctctctg gcatctctga aatcatcccc gagatggaga tctgcgattt tgacttcgaa    1080
ccctgtggct actccatgaa tgcgatccat ggctctgcat tctccacaat ccatgtgacg    1140
```

```
cccgaggacg gtttcagcta cgccagttac gaggttatgg gcttggatgc cactgctctg    1200
tcttatggtg accttgtcaa gagggtcctc cggtgctttg gcccctcaga gttttccgtt    1260
gccgtgacca tcttcggcgg gcgtggccat gccgggacat ggggaaaggc acttggtgca    1320
gaggtctatg actgcaacaa catggtggag caggagctgc ctggaggcgg gctcctcgtg    1380
taccagagct tctgtgctgc tgaagacgct gttgctacct cgcccaaatc tgttttccac    1440
tgctttgacg gcgagaacgt ggagagtgct cctcctccta tgaagaagga ctacaagctg    1500
gctaatcttc tctgctggga ggaggaagcg gatgccatgg aggagaaggc gggagtgctt    1560
gatgagtaag acgggcttct ggggtcgatt tgcttctgag ttgtttattt tatatcgtcg    1620
caatttcgtg gttgtcgttt ggttattctg tgaagcagcc aagccaggct attgttatga    1680
aaatttgtcg tctgtaagca tgtgaacttc cgatgttgcc acatgctgga tcagtctgaa    1740
taagtaagta tgcagctcta ggtggtcagc tgcgtctacc acaatgagca tgaacgtatg    1800
gagaaatatc tgtgaacccc atttggttta tgaataagat ttgttttttcc cgagttaaaa    1860 aaaaaaaaaa aaa                                                      1873

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tacccagagc aaccaatggt taaccttgag atgtgcatga                           40

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
taaccttgag atgtgcatga                                                 20

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggaacacca gttcttgggc tctcctcctc ctcctcctcc tcatgcacat ctcaaggtta     60

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tacccagagc aaccaatggt                                                 20
```

-continued

```
<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accattggtt gctctgggta agctcgacca ggtcctgg                                  38
```